United States Patent [19]

Janssens et al.

[11] Patent Number: 4,943,580

[45] Date of Patent: Jul. 24, 1990

[54] ANTI-HISTAMINIC BENZIMIDAZOLE, IMIDAZOPYRIDINE AND PURINE DERIVATIVES

[75] Inventors: Frans E. Janssens, Bonheiden; Gaston S. M. Diels, Ravels; Joseph L. G. Torremans, Beerse; Francois M. Sommen, Wortel, all of Belgium

[73] Assignee: Janssen Pharmaceutica N.V., Beerse, Belgium

[21] Appl. No.: 307,712

[22] Filed: Feb. 6, 1989

Related U.S. Application Data

[63] Continuation of Ser. No. 155,465, Feb. 12, 1988, abandoned, which is a continuation-in-part of Ser. No. 23,739, Mar. 9, 1987, abandoned.

[51] Int. Cl.$^5$ .................... A61K 31/44; C07D 471/04
[52] U.S. Cl. .................... 514/303; 514/212; 514/261; 514/269; 514/275; 514/306; 514/322; 514/395; 540/597; 540/603; 544/61; 544/105; 544/127; 544/237; 544/255; 544/262; 544/263; 544/265; 544/268; 544/277; 544/278; 544/280; 544/282; 544/284; 544/310; 544/316; 544/319; 544/405; 544/264; 544/327; 544/328; 544/331; 544/333; 544/281; 546/114; 546/115; 546/118; 546/199; 546/271; 548/327; 548/181; 548/213; 548/214

[58] Field of Search ............... 546/118, 199, 114, 115; 544/255, 61, 105, 127, 255, 237, 263, 268, 277, 278, 316, 281, 282, 284, 310, 319, 331, 262, 265, 316, 405; 540/597, 603; 548/327; 514/261, 212, 269, 275, 303, 306, 322, 395

[56] References Cited

U.S. PATENT DOCUMENTS

| 4,219,559 | 8/1980 | Janssens et al. ............. 424/267 |
| 4,556,660 | 12/1985 | Janssens et al. ............. 514/272 |
| 4,588,722 | 5/1986 | Janssens et al. ............. 514/228 |
| 4,634,704 | 1/1987 | Janssens et al. ............. 514/253 |
| 4,695,569 | 9/1987 | Janssens et al. ............. 514/258 |

FOREIGN PATENT DOCUMENTS

151826 8/1985 European Pat. Off. .
206415 12/1986 European Pat. Off. .

OTHER PUBLICATIONS

J. of Heterocyclic Chem., 24, 31 (1987), pp. 31–37.
J. Med. Chem. 1985, 28, pp. 1925–1933.

*Primary Examiner*—Mary C. Lee
*Assistant Examiner*—Bernard I. Dentz
*Attorney, Agent, or Firm*—Charles J. Metz

[57] ABSTRACT

Novel 1-alkyl substituted benzimidazole derivatives and their pharmaceutically acceptable acid addition salts having anti-histaminic properties, compositions containing the same, and methods of treating allergic diseases in warm-blooded animals.

14 Claims, No Drawings

ANTI-HISTAMINIC BENZIMIDAZOLE, IMIDAZOPYRIDINE AND PURINE DERIVATIVES

CROSS-REFERENCE TO RELATED APPLICATIONS

This application is a continuation of U.S. Ser. No. 155,465 filed Feb. 12, 1988, now abandoned, which is a continuation-in-part of our application Ser. No. 23,739 filed Mar. 9, 1987 now abandoned.

BACKGROUND OF THE INVENTION

In U.S. Pat. No. 4,219,559 there are described a number of 1-substituted N-heterocyclyl-4-piperidinamines as compounds having useful anti-histaminic properties.

In U.S. Pat. Nos. 4,556,660, 4,634,704, 4,695,569 and 4,588,722 there are described further series of N-heterocyclyl-4-piperidinamines as compounds having useful anti-histaminic and serotonin-antagonistic properties.

Further there are described in the Eur. Pat. Publ. No. 151,826 published Aug. 21, 1985, which corresponds to U.S. Ser. No. 671,135 a number of 4-(bicyclic heterocyclyl)methyl and -heteropiperidines having useful anti-histaminic and serotonin-antagonistic properties. In addition some anti-histaminic (4-piperidinylmethyl and -hetero)purines have been described in the Eur. Pat. Publ. No. 206,415 published Dec. 30, 1986, which corresponds to U.S. Ser. No. 858,339.

Finally, some anti-histaminic N-1H-benzimidazole-4-piperidinamines have been described in J. Heterocyclic Chem., 24, 31 (1987).

The compounds of the present invention differ therefrom by the fact that the benzimidazole derivative is invariably substituted in the 1-position with a hydroxy-, mercapto- or amino-$C_{1-6}$alkyl group, which is optionally O, S or N-alkylated, and by their favourable pharmacological properties.

DESCRIPTION OF THE PREFERRED EMBODIMENTS

This invention is concerned with novel 1-alkyl substituted benzimidazole derivatives which can structurally be represented by the formula

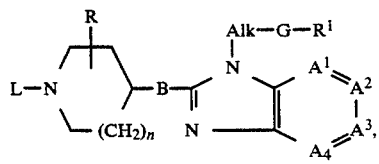

the pharmaceutically acceptable acid addition salts and the stereo-chemically isomeric forms thereof, wherein
—$A^1$=$A^2$—$A^3$=$A^4$— is a bivalent radical having the formula —CH=CH—CH=CH— (a-1), —N=CH—CH=CH— (a-2), —CH=N—CH=CH— (a-3), —CH=CH—N=CH— (a-4), —CH=CH—CH=N— (a-5), —N=CH—N=CH— (a-6), or —CH=N—CH=N— (a-7);

wherein one or two hydrogen atoms in said radicals (a-1)–(a-7) may, each independently from each other, be replaced by halo, $C_{1-6}$alkyl, $C_{1-6}$alkyloxy, trifluoromethyl or hydroxy;

$R^1$ is hydrogen, $C_{2-6}$alkenyl optionally substituted with $Ar^2$, $C_{3-6}$alkynyl, $Ar^1$, or $C_{1-6}$alkyl optionally substituted with $Ar^1$, hydroxy, $C_{1-6}$alkyloxy, carboxyl, $C_{1-6}$alkyloxycarbonyl, $Ar^2$-oxycarbonyl or $Ar^2$-$C_{1-6}$alkyloxycarbonyl;

G is O, S or $NR^2$; said $R^2$ being hydrogen, $C_{1-6}$alkyl, $C_{1-6}$alkylcarbonyl, $C_{1-6}$alkyloxycarbonyl or $Ar^2$-$C_{1-6}$alkyl;

B is $NR^3$, $CH_2$, O, S, SO or $SO_2$; said $R^3$ being hydrogen, $C_{1-6}$alkyl, $C_{3-6}$cycloalkyl, $C_{1-6}$alkylcarbonyl, $C_{1-6}$alkyloxycarbonyl or $Ar^2$-$C_{1-6}$alkyl;

R is hydrogen or $C_{1-6}$alkyl;

n is 0, 1 or 2;

L is hydrogen, $C_{1-6}$alkylcarbonyl, $C_{1-6}$alkylsulfonyl, $C_{1-6}$alkyloxycarbonyl, $Ar^2$-$C_{1-6}$alkyloxycarbonyl, $Ar^2$-carbonyl, $Ar^2$-sulfonyl, $C_{3-6}$cycloalkyl, $C_{2-6}$alkenyl optionally substituted with $Ar^2$, $C_{1-12}$alkyl, a radical of formula

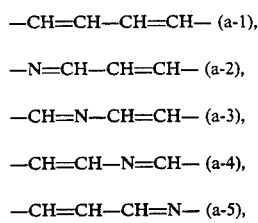

$R^4$ is $Ar^2$, Het, cyano, isocyanato, isothiocyanato, $Ar^2$-sulfonyl or halo;

$R^5$ is hydrogen, $Ar^2$, Het or $C_{1-6}$alkyl optionally substituted with halo, $Ar^2$ or Het;

$R^6$ is hydrogen, $Ar^2$, Het or $C_{1-6}$alkyl optionally substituted with halo, $Ar^2$ or Het;

$R^7$ is $Ar^2$ or naphthalenyl;

Y is O, S, $NR^8$; said $R^8$ being hydrogen, $C_{1-6}$alkyl, $C_{1-6}$alkylcarbonyl or $Ar^1$-carbonyl;

$Z^1$ and $Z^2$ each independently are O, S, $NR^9$ or a direct bond; said $R^9$ being hydrogen or $C_{1-6}$alkyl;

X is O, S or $NR^{10}$; said $R^{10}$ is hydrogen, $C_{1-6}$alkyl or cyano;

each Alk independently being $C_{1-6}$alkanediyl;

Het is a five- or six-membered heterocyclic ring containing a number of heteroatoms which varies of from 1 to 4, said heteroatoms being selected from the group consisting of oxygen, sulfur and nitrogen, provided that no more than two oxygens or sulfurs are present, said five or six-membered ring being optionally condensed with a five- or six-membered carbocyclic or heterocyclic ring also containing 1, 2, 3 or 4 heteroatoms, the latter heteroatoms being selected from the group consisting of oxygen, sulfur and nitrogen, provided that no more than 2 oxygens or sulfurs are present, and when said Het is a bicyclic ring system it may optionally be substituted with up to 6 substituents, and when said Het is a monocyclic ring system it may optionally be substituted with up to 3 substituents, said substituents of Het being selected from the group consisting of a bivalent radical of formula =X; halo; isocyanato; isothiocyanato; nitro; cyano; trifluoromethyl; a radical of formula —A; a radical of formula —Y—A; or a radical of formula —$Z^1$—C(=X)—$Z^2$—A; wherein said =X independently has the same meaning of the previously defined X and A is hydrogen, $Ar^2$ or $C_{1-6}$alkyl being optionally substituted with $Ar^2$, $C_{1-6}$alkyloxy, $Ar^2$—O, hydroxy, or $C_{1-6}$alkyloxycarbonyl; and Y, $Z^1$ and $Z^2$ independently have the same meaning of the previously defined Y, $Z^1$ and $Z^2$; provided that (i) when in the radical —Y—A, A is hydrogen, then Y is other than a direct bond, or (ii) when in the radical —$Z^1$—C(=X)—$Z^2$—A, A is hydrogen and $Z^1$ is $NR^9$, O or S, then $Z^2$ is other than O or S; preferably the sum of heteroatoms in the above defined Het is less than 6;

$Ar^1$ is a member selected from the group consisting of phenyl, being optionally substituted with 1, 2 or 3 substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl; thienyl; halothienyl; furanyl; $C_{1-6}$alkyl substituted furanyl; pyridinyl; pyrimidinyl; pyrazinyl; thiazolyl and imidazolyl optionally substituted with $C_{1-6}$alkyl; and $Ar^2$ is a member selected from the group consisting of phenyl being optionally substituted with up to three substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$ alkyl)amino, carboxyl, $C_{1-6}$alkyloxycarbonyl and $C_{1-6}$ alkylcarbonyl.

As used in the foregoing definitions the term halo is generic to fluoro, chloro, bromo and iodo; the term "$C_{1-6}$alkyl" is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "$C_{1-12}$alkyl" is meant to include $C_{1-6}$alkyl radicals, as defined hereinabove, and the higher homologs thereof having from 7 to 12 carbon atoms; the term "$C_{3-6}$cycloalkyl" is generic to cyclopropyl, cyclobutyl, cyclopentyl and cyclohexyl. "$C_{2-6}$alkenyl" defines straight and branch chained hydrocarbon radicals containing one double bond and having from 2 to 6 carbon atoms such as, for example, ethenyl, 2-propenyl, 3-butenyl, 2-butenyl, 2-pentenyl, 3-pentenyl, 3-methyl-2-butenyl and the like; "$C_{3-6}$alkynyl" defines straight and branch chained hydrocarbon radicals containing one triple bond and having from 3 to 6 carbon atoms such as, for example, 2-propynyl, 2-butynyl, 3-butynyl, 2-pentynyl, 3-pentynyl, 4-pentynyl and the like; and when a $C_{3-6}$alkenyl or a $C_{3-6}$alkynyl is substituted on a heteroatom, then the carbon atom of said $C_{3-6}$alkenyl or said $C_{3-6}$alkynyl connected to said heteroatom preferably is saturated.

It is to be understood that the compounds of formula (I) may exist in hydrated or in solvent addition forms and that the invention includes all such forms.

In particularly Het is (i) an optionally substituted five- or six-membered heterocyclic ring containing 1, 2, 3 or 4 heteroatoms selected from the group consisting of oxygen, sulfur and nitrogen, provided that no more than two oxygens or sulfurs are present; or Het is (ii) an optionally substituted five- or six-membered heterocyclic ring containing 1 or 2 heteroatoms selected from the group consisting of oxygen, sulfur and nitrogen, being ortho-condensed with an optionally substituted five- or six-membered ring through two ring carbon atoms or one ring carbon and one ring nitrogen atom, containing in the remainder of the condensed ring only carbon atoms; or Het is (iii) an optionally substituted five- or six-membered heterocyclic ring containing 1 or 2 heteroatoms selected from the group consisting of oxygen, sulfur and nitrogen, being ortho-condensed with an optionally substituted five- or six-membered heterocyclic ring through two ring carbon atoms or one ring carbon and one ring nitrogen atom, containing in the remainder of the condensed ring 1 or 2 heteroatoms selected from the group consisting of oxygen, sulfur and nitrogen, when said Het is a monocyclic ring system it may optionally be substituted with up to 2 substituents, and when said Het is a bicyclic ring system it may be substituted with up to 5 substituents, said substituents being the same as previously described.

In more detail Het is a member selected from the group consisting of pyridinyl which is optionally substituted with one or two substituents each independently selected from halo, amino, mono- and di($C_{1-6}$alkyl)amino, $Ar^2$—$C_{1-6}$alkylamino, nitro, cyano, aminocarbonyl, $C_{1-6}$alkyl, $C_{1-6}$alkyloxy, $C_{1-6}$alkylthio, $C_{1-6}$alkyloxycarbonyl, hydroxy, $C_{1-6}$alkylcarbonyloxy, $Ar^2$—$C_{1-6}$alkyl and carboxyl; pyridinyloxide optionally substituted with nitro; pyrimidinyl which is optionally substituted with one or two substituents each independently selected from the group consisting of halo, amino, hydroxy, $C_{1-6}$alkyl, $C_{1-6}$alkyloxy, $C_{1-6}$alkylthio and $Ar^2$—$C_{1-6}$alkyl; pyridazinyl which is optionally substituted with $C_{1-6}$alkyl or halo; pyrazinyl which is optionally substituted with halo, amino or $C_{1-6}$alkyl; thienyl which is optionally substituted with halo or $C_{1-6}$alkyl; furanyl which is optionally substituted with halo or $C_{1-6}$alkyl; pyrrolyl which is optionally substituted with $C_{1-6}$alkyl; thiazolyl which is optionally substituted with $C_{1-6}$alkyl, $C_{1-6}$alkyloxycarbonyl, $Ar^2$ or $Ar^2$—$C_{1-6}$alkyl; imidazolyl which is optionally substituted with one or two substituents each independently selected from $C_{1-6}$alkyl and nitro; tetrazolyl which is optionally substituted with $C_{1-6}$alkyl; 1,3,4-thiadiazolyl which is optionally substituted with $C_{1-6}$alkyl; 5,6-dihydro-4$\underline{H}$-1,3-thiazin-2-yl which is optionally substituted with $C_{1-6}$alkyl; 4,5-dihydrothiazolyl which is optionally substituted with $C_{1-6}$alkyl; oxazolyl which is optionally substituted with $C_{1-6}$alkyl; 4,5-dihydro-5-oxo-1$\underline{H}$-tetrazolyl which is optionally substituted with $C_{1-6}$alkyl; 1,4-dihydro-2,4-dioxo-3(2$\underline{H}$)-pyrimidinyl being optionally substituted with $C_{1-6}$alkyl; 4,5-dihydro-4-oxo-2-pyrimidinyl; 2-oxo-3-oxazolidinyl; indolyl which is optionally substituted with $C_{1-6}$alkyl; quinolinyl which is optionally substituted with hydroxy or $C_{1-6}$alkyl; quinazolinyl which is optionally substituted with hydroxy or $C_{1-6}$alkyl; quinoxalinyl which is optionally substituted with $C_{1-6}$alkyl; phthalazinyl which is optionally substituted with halo; 1,3-dioxo-1$\underline{H}$-isoindol-2-(3$\underline{H}$)-yl; 2,3-dihydro-3-oxo-4$\underline{H}$-benzoxazinyl and 2,3-dihydro-1,4-benzodioxinyl, both being optionally substituted with $C_{1-6}$alkyl or halo; dioxanyl being optionally substituted with $C_{1-6}$alkyl; 2-oxo-2$\underline{H}$-1-benzopyranyl and 4-oxo-4$\underline{H}$-1-benzopyranyl both being optionally substituted with $C_{1-6}$alkyl; morfolinyl; thiomorfolinyl; piperidinyl; a radical of formula

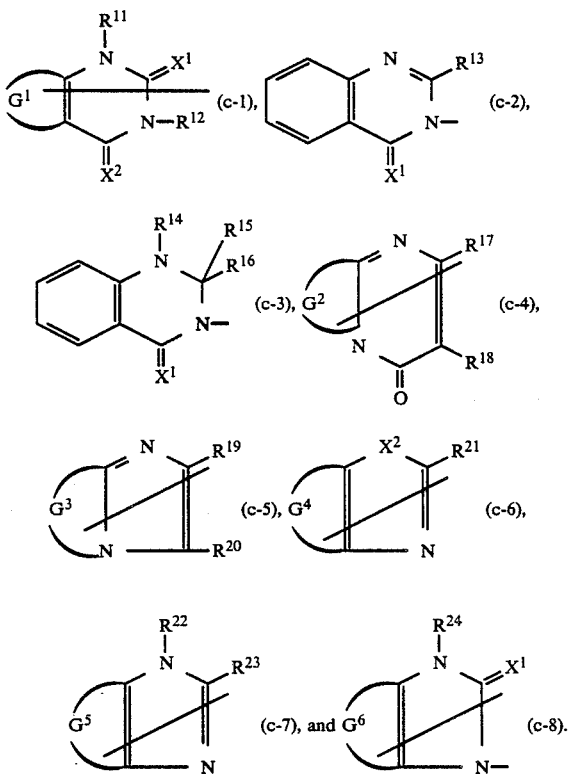

wherein $X^1$ and $X^2$ are each independently O or S; $R^{11}$, $R^{12}$, $R^{14}$, $R^{22}$ and $R^{24}$ are each independently hydrogen, $C_{1-6}$alkyl, $Ar^2$—$C_{1-6}$alkyl, hydroxy$C_{1-6}$alkyl or $C_{1-6}$alkyloxycarbonyl; $R^{13}$, $R^{15}$, $R^{16}$, $R^{17}$, $R^{18}$, $R^{19}$, $R^{20}$, $R^{21}$ and $R^{23}$ are each independently hydrogen, $C_{1-6}$alkyl, hydroxy, mercapto, $C_{1-6}$alkyloxy, $C_{1-6}$alkylthio, halo and ($C_{1-6}$alkyloxycarbonyl)$C_{1-6}$alkyl; $G^1$ is —CH=CH—CH=CH—, —S—CH=CH— or —N=CH—NH—; $G^2$ is —CH=CH—CH=CH—, —S—(CH$_2$)$_2$—, —S—(CH$_2$)$_3$—, —(CH$_2$)$_4$— or —S—CH=CH—; $G^3$ is —CH=CH—CH=CH—, —CH$_2$—NH—(CH$_2$)$_2$—, —S—CH=CH—, —N=CH—CH=CH—, —CH=N—CH=CH—, —CH=CH—N=CH—, —CH=CH—CH=N—, —N=CH—N=CH— or —CH=N—CH=N—; $G^4$ is —CH=CH—CH=CH—, —CH$_2$—NH—(CH$_2$)$_2$—, —N=CH—CH=CH—, —CH=N—CH=CH—, —CH=CH—N=CH—, —CH=CH—CH=N—, —N=CH—N=CH— or —CH=N—CH=N—; $G^5$ is —CH=CH—CH=CH—, —N=CH—CH=CH—, —CH=N—CH=CH—, —CH=CH—N=CH—, —CH=CH—CH=N—, —N=CH—N=CH— or —CH=N—CH=N—; $G^6$ is —CH=CH—CH=CH—, —N=CH—CH=CH—, —CH=N—CH=CH—, —CH=CH—N=CH—, —CH=CH—CH=N—, —N=CH—N=CH— or —CH=N—CH=N—;

wherein one or two hydrogen atoms in said radicals $G^1$, $G^2$, $G^3$, $G^4$, $G^5$ or $G^6$ or in the benzene part of the radicals of formula (c-2) or (c-3) may be replaced by $C_{1-6}$alkyl, $C_{1-6}$alkylthio, $C_{1-6}$alkyloxy or halo where said hydrogen atom is bonded on a carbon atom, or by $C_{1-6}$alkyl, $C_{1-6}$alkyloxycarbonyl, $Ar^2$—$C_{1-6}$alkyl, where said hydrogen is bonded on a nitrogen atom;

$R^{11}$, $R^{12}$, $R^{17}$, $R^{18}$, $R^{19}$, $R^{20}$, $R^{21}$, $R^{22}$ or $R^{23}$ being absent where the radical of formula (c-1), (c-4), (c-5), (c-6) or (c-7) respectively is connected to Alk on the atom bearing said $R^{11}$, $R^{12}$, $R^{17}$, $R^{18}$, $R^{19}$, $R^{20}$, $R^{21}$, $R^{22}$ or $R^{23}$.

A particular group among the compounds of formula (I) comprises the compounds of formula (I) provided that when (i) L is hydrogen, $C_{1-6}$alkyl or benzyl and (ii) $R^1$—G—Alk is $C_{1-6}$alkyloxyethyl, $C_{2-6}$alkenyloxyethyl, $C_{3-6}$alkynyloxyethyl or phenoxyethyl then —$A^1$=$A^2$—$A^3$=$A^4$— is other than a bivalent radical of formula (a-1).

An interesting subgroup among the compounds of formula (I) comprises those compounds of formula (I) wherein —$A^1$=$A^2$—$A^3$=$A^4$— is a bivalent radical having the formula (a-1).

Another interesting subgroup among the compounds of formula (I) comprises those compounds of formula (I) wherein —$A^1$=$A^2$—$A^3$=$A^4$— is a bivalent radical having a formula (a-2) through (a-7), with (a-2) being the most interesting subgroup.

Among the above subgroups those compounds of formula (I) are preferred wherein Het is the particular Het described hereinabove.

Particularly preferred compounds within the invention are those preferred compounds within the invention wherein $R^1$ is hydrogen, $C_{2-6}$alkenyl, $C_{3-6}$alkynyl, $Ar^1$ or $C_{1-6}$alkyl optionally substituted with carboxyl, G is O, L is hydrogen, $C_{1-6}$alkyl or a radical of formula (b-1), (b-2) or (b-3) and B is NH or $CH_2$.

Especially preferred compounds within the invention are those particularly preferred compounds wherein $R^4$, $R^5$ and $R^6$ are each $Ar^2$ or Het and $R^1$ is $C_{1-3}$alkyl optionally substituted with carboxyl, 2-propenyl or 2-propynyl.

More especially preferred compounds are selected from the group consisting of 3-(2-ethoxyethyl)-N-(1-methyl-4-piperidinyl)-3H-imidazo[4,5-b]pyridin-2-amine and 3-(2-ethoxyethyl)-N-[1-[2-(4-methoxyphenyl)ethyl]-4-piperidinyl]-3H-imidazo-[4,5-b]pyridin-2-amine, the pharmaceutically acceptable acid addition salts and the possible stereochemically isomeric forms thereof.

The compounds of formula (I) can generally be prepared by reacting an intermediate of formula (II) with a diamine of formula (III).

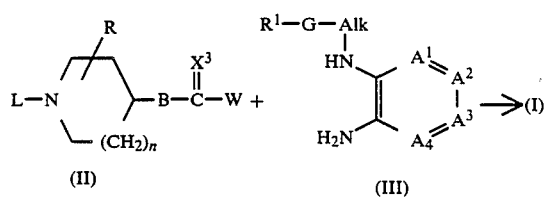

In some instances the reaction of (II) with (III) first yields an intermediate of formula (II-a)

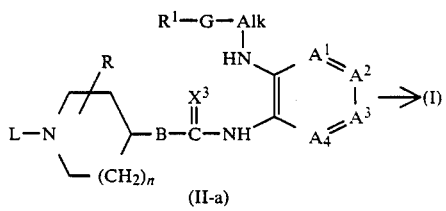

which may in situ or, if desired, after isolating and purifying it, be cyclisized to obtain the desired compounds of formula (I).

In the foregoing and following reaction schemes W and $W^1$ represent an appropriate leaving group such as, for example, halo, e.g., chloro, bromo or iodo, or a sulfonyloxy group, e.g., methylsulfonyloxy or 4-methylphenylsulfonyloxy, whereas W may also be alkyloxy, alkylthio, $Ar^2$—O— or $Ar^2$—S—. $X^3$ in formulae (II) and (II-a) represents O, S or NH.

The piperidine, pyrrolidine or hexahydro-1H-azepine derivatives of formula (II) may in situ be generated, for example, by converting a piperidine, pyrrolidine or hexahydro-1H-azepine which is substituted with a —B—C(=$X^3$)—OH radical into an intermediate of formula (II) by reacting the former with thionyl chloride, phosphor trichloride, phosphoryl chloride, polyphosphoric acid, phosphoroxy chloride and the like.

The reaction of (II) with (III) may be conducted in a suitable solvent such as, for example, a hydrocarbon, e.g., benzene, hexane; an ether, e.g., 1,1'-oxybisethane, tetrahydrofuran; a ketone, e.g., 2-propanone, 2-butanone; an alcohol, e.g., methanol, ethanol, 2-propanol, 1-butanol; a halogenated hydrocarbon, e.g., trichloromethane, dichloromethane, an organic acid, e.g., acetic acid, propanoic acid; a polar aprotic solvent, e.g., N,N-dimethylformamide, N,N-dimethylacetamide and the like; and mixtures of such solvents. Depending upon the solvent and nature of W it may be appropriate to add a suitable base and/or a iodide salt, preferably an alkali metal iodide, to the reaction mixture. Elevated temperatures may enhance the reaction rate.

The compounds of formula (I) can also be prepared by reacting an intermediate of formula (V) with an intermediate of formula (IV) wherein $E^1$ and $E^2$ are selected so that during the reaction a bivalent radical —B— is formed.

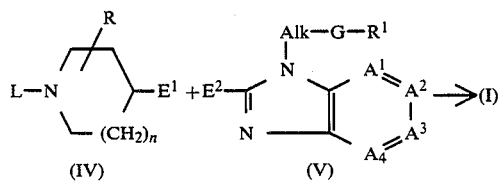

For example, the compounds of formula (I) can be prepared by reacting an intermediate of formula (IV) wherein $E^1$ is a radical of formula —B—M with an intermediate of formula (V) wherein $E^2$ is a radical W.

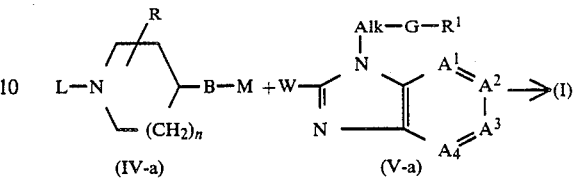

In (IV-a) M is, depending upon the nature of B, hydrogen or an appropriate alkalimetal or earth alkaline metal and in (V-a) W has the previously described meanings. Additionally, the compounds of formula (I) can also be prepared by reacting an intermediate of formula (IV) wherein $E^1$ is $W^1$ with an intermediate of formula (V) wherein $E^2$ is a radical of formula —B—M, said $W^1$ and M having the previously described meanings.

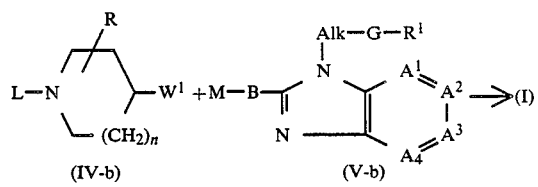

More particularly, the compounds of formula (I) wherein B is —$CH_2$— can also be prepared by reacting an intermediate of formula (IV) wherein $E^1$ represents a radical of formula —$CH_2$—$W^1$, (IV-c), with an intermediate of formula (V) wherein $E^2$ represents M, (V-c) or alternatively, by reacting an intermediate of formula (IV), wherein $E^1$ is a radical of formula —M, (IV-d), with an intermediate of formula (V) wherein $E^2$ is a radical of formula —$CH_2$—$W^1$, (V-d).

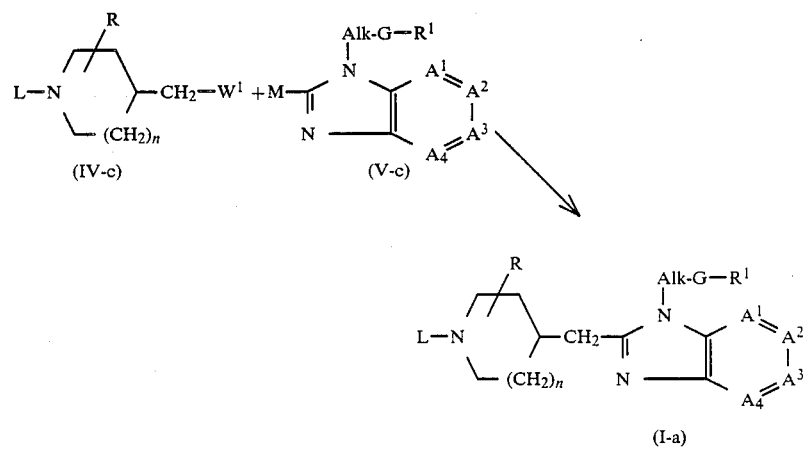

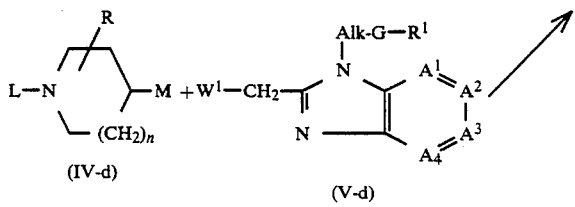

The reactions of (IV-a) with (V-a), (IV-b) with (V-b), (IV-c) with (V-c) and (IV-d) with (V-d) may conveniently be conducted in an appropriate solvent such as, for example, an aromatic hydrocarbon, e.g., benzene, methylbenzene; an ether, e.g., 1,4-dioxane, 1,1'-oxybisethane, tetrahydrofuran and the like; a halogenated hydrocarbon, e.g., trichloromethane and the like; N,N-dimethylformamide (DMF); N,N-dimethylacetamide (DMA); and where M is hydrogen, said solvent may also be a $C_{1-6}$alkanol, e.g., methanol, ethanol, 1-butanol and the like; a ketone, e.g., 2-propanone, 4-methyl-2-pentanone and the like. In some instances, the addition of an appropriate base such as, for example, an alkali metal carbonate or hydrogen carbonate, sodium hydride or an organic base such as, for example, N,N-diethylethanamine or N-(1-methylethyl)-2-propanamine and/or the addition of a iodide salt, preferably an alkali metal iodide, may be appropriate. Somewhat elevated temperatures may enhance the rate of the reaction.

Or, the compounds of formula (I) wherein B is —$NR^3$— can also be prepared by reacting an intermediate of formula (IV) wherein $E^1$ is an oxo radical, (IV-e), with an intermediate of formula (V) wherein $E^2$ represents a radical —$NHR^3$, (V-e).

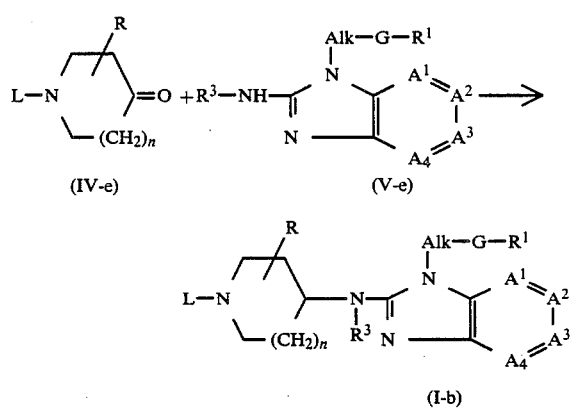

The reaction of (IV-e) with (V-e) is conveniently carried out by treating a mixture of the reactants in a suitable reaction-inert organic solvent with an appropriate reductant. Preferably, the 3-pyrrolidinone, 4-piperidinone or hexahydro-1H-azepine-4-one of formula (IV-e) is first reacted with the benzimidazolamine of formula (V-e) to form an enamine, which optionally may be isolated and further purified, and subsequently subjecting the said enamine to a reduction reaction. Suitable solvents are, for example, water; $C_{1-6}$ alkanols, e.g., methanol, ethanol, 2-propanol and the like; cyclic ethers, e.g., 1,4-dioxane and the like; halogenated hydrocarbons, e.g., trichloromethane and the like; N,N-dimethylformamide; N,N-dimethylacetamide; dimethyl sulfoxide and the like; or a mixture of such solvents. Appropriate reductants are for example, metal or complex metal hydrides, e.g., sodium borohydride, lithium aluminiumhydride; or hydrogen, the latter being preferably used in the presence of a suitable catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene and the like.

The compounds of formula (I) wherein B is —NH— can also be prepared by a cyclodesulfurization reaction of an appropriate thiourea derivative of formula (VII), which may in situ be formed by condensing an isothiocyanate of formula (VI) with a diamine of formula (III).

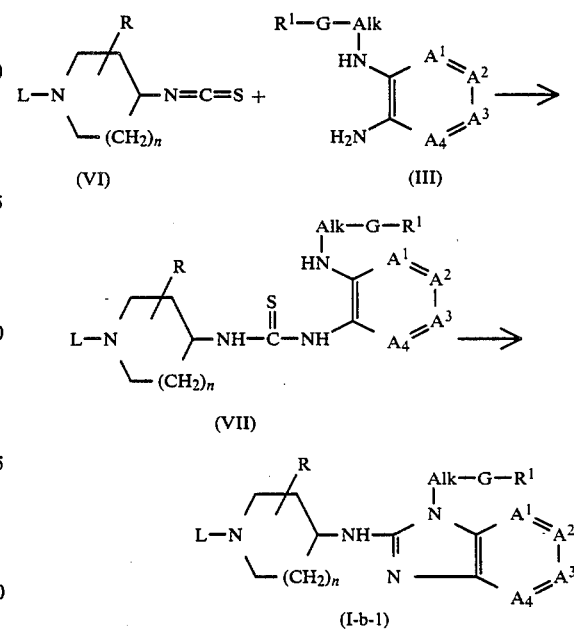

Said cyclodesulfurization reaction may be carried out by the reaction of (VII) with an appropriate alkyl halide, preferably iodomethane in a suitable reaction-inert organic solvent, e.g., a lower alkanol such as, methanol, ethanol, 2-propanol and the like. Otherwise, the cyclodesulfurization reaction may be carried out by the reaction of (VII) with an appropriate metal oxide or salt in a suitable solvent according to art-known procedures. For example, the compounds of formula (I-b-1) can easily be prepared by the reaction of (VII) with a Hg(II) or Pb(II) oxide or salt such as, for example, HgO, $HgCl_2$, $Hg(OAc)_2$, PbO or $Pb(OAc)_2$. In certain instances it may be appropriate to supplement the reaction mixture with a small amount of sulfur. Even so methanediimines, especially dicyclohexylcarbodiimide may be used as cyclodesulfurizing agents.

The compounds of formula (I) can also be prepared by N-alkylating an intermediate of formula (VIII) with an appropriate reagent of formula (IX).

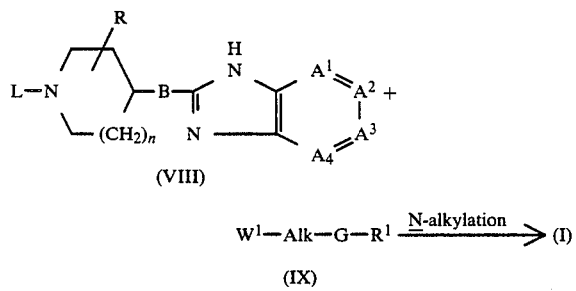

(VIII)

$W^1$—Alk—G—$R^1$ $\xrightarrow{\text{N-alkylation}}$ (I)

(IX)

The N-alkylation reaction is conveniently conducted in an inert organic solvent such as, for example, an aromatic hydrocarbon, e.g., benzene, methylbenzene, dimethylbenzene, and the like; an alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a polar aprotic solvent, e.g., N,N-dimethylformamide (DMF), N,N-dimethylacetamide (DMA), dimethyl sulfoxide (DMSO), nitrobenzene, 1-methyl-2-pyrrolidinone, and the like. The addition of an appropriate base such as, for example, an alkali or an earth alkaline metal carbonate, hydrogen carbonate, hydroxide, and oxide, e.g., sodium carbonate, sodium hydrogen carbonate, potassium carbonate, sodium hydroxide, calcium carbonate, calcium hydroxide, calcium oxide and the like, or an organic base, such as, for example, a tertiary amine, e.g., N,N-diethylethanamine, N-(1-methylethyl)-2-propanamine, 4-ethylmorpholine and the like may be utilized to pick up the acid which is liberated during the course of the reaction. In some instances the addition of a iodide salt, preferably an alkali metal iodide, is appropriate. Somewhat elevated temperatures may enhance the rate of the reaction.

The compounds of formula (I) can also be converted into each other. Some examples of such conversions will be described hereinafter.

In order to simplify the structural representations of the compounds of formula (I) and of certain precursors and intermediates thereof the

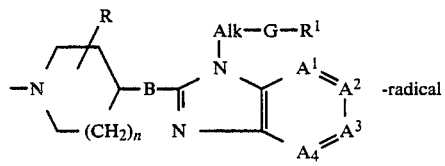

will hereafter be represented by the symbol D.

The compounds of formula (I) wherein L is other than hydrogen, said L being represented by $L^1$, and said compounds being represented by formula (I-c) can generally be prepared by N-alkylating a compound of formula (I) wherein L is hydrogen, said compounds being represented by formula (I-d), with a reagent of formula (X).

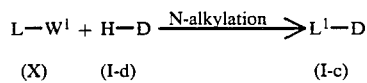

The said N-alkylation is conveniently carried out according to art-known N-alkylation procedures described hereinabove for the preparation of (I) starting from (VIII) and (IX).

The compounds of formula (I) wherein L is $C_{3-6}$cycloalkyl, $C_{1-12}$alkyl, a radical of formula (b-1), (b-2) or (b-3) said radical L being represented by the radical $L^2H$—, and said compounds being represented by formula (I-c-1) can also be prepared by the reductive N-alkylation reaction of (I-d) with an appropriate ketone or aldehyde of formula $L^2$=O (XI), said $L^2$=O being an intermediate of formula $L^2H_2$ wherein two geminal hydrogen atoms are replaced by =O, and $L^2$= is a geminal bivalent radical comprising $C_{3-6}$cycloalkylidene, $C_{1-12}$alkylidene, $R^4$—$C_{1-6}$alkylidene, $R^5$—Y—$C_{1-6}$alkylidene and $R^6$—$Z^2$—C(=X)—$Z^1$—$C_{1-6}$alkylidene.

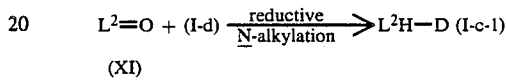

Said reductive N-alkylation reaction may conveniently be carried out by catalytically hydrogenating a stirred and heated mixture of the reactants in a suitable reaction inert organic solvent according to art-known catalytic hydrogenating procedures. Suitable solvents are, for example, water; alkanols, e.g., methanol, ethanol, 2-propanol and the like; cyclic ethers, e.g., 1,4-dioxane and the like; halogenated hydrocarbons, e.g., trichloromethane and the like; N,N-dimethylformamide; dimethyl sulfoxide and the like; or a mixture of two or more of such solvents. The term "art-known catalytic hydrogenating procedures" means that the reaction is carried out under hydrogen atmosphere in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene and the like.

The compounds of formula (I) wherein L is a radical of formula (b-2) wherein $R^5$ is $Ar^2$ or Het, said $R^5$ being represented by $R^{5-a}$ and said compounds by formula (I-c-2) may also be prepared by alkylating a compound of formula (I) wherein L is a radical of formula (b-2) wherein $R^5$ is hydrogen, said compounds being represented by formula (I-c-3), with a reagent of formula (XII).

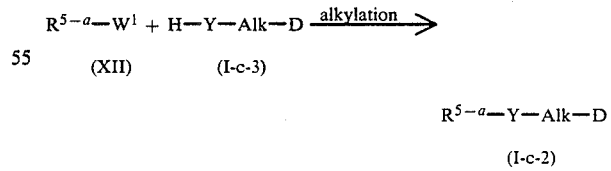

The compounds of formula (I-c-2) can also be prepared by alkylating a compound of formula (I-c-4) with a reagent of formula (XIII).

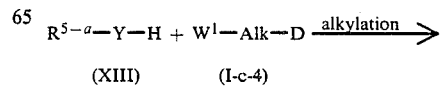

R⁵⁻ᵃ—Y—Alk—D (I-c-2)

The alkylation reactions of (XII) with (I-c-3) and (XIII) with (I-c-4) may conveniently be conducted in an inert organic solvent such as, for example, an aromatic hydrocarbon, e.g., benzene, methylbenzene, dimethylbenzene; a ketone, e.g., 2-propanone, 4-methyl-2-pentanone; an ether, e.g., 1,4-dioxane, 1,1'-oxybisethane, tetrahydrofuran; and a polar aprotic solvent, e.g., N,N-dimethylformamide (DMF); N,N-dimethylacetamide (DMA); dimethyl sulfoxide (DMSO); nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. Somewhat elevated temperatures may enhance the rate of the reaction.

The compounds of formula (I) wherein L is a radical of formula (b-3) wherein $Z^1$ is NH and $Z^2$ is other than a direct bond, said $Z^2$ being represented by $Z^{2-a}$, and said compounds by (I-c-5) can be prepared by reacting an isocyanate or isothiocyanate of formula (I-c-6) with a reagent of formula (XIX).

R⁶—Z²⁻ᵃ—H + X=C=N—Alk—D ⟶

(XIV)        (I-c-6)

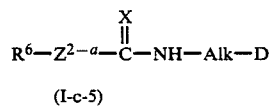

(I-c-5)

The compounds of formula (I) wherein L is a radical of formula (b-3) wherein $Z^2$ is NH and $Z^1$ is other than a direct bond, said $Z^1$ being represented by $Z^{1-a}$ and said compounds by (I-c-7), can be prepared by reacting a isocyanate or isothiocyanate of formula (XV) with a compound of formula (I-c-8).

R⁶—N=C=X + H—Z¹⁻ᵃ—Alk—D ⟶

(XV)         (I-c-8)

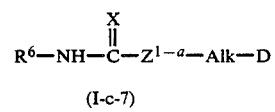

(I-c-7)

The reaction of (XIV) with (I-c-6), or (XV) with (I-c-8) is generally conducted in a suitable reaction-inert solvent such as, for example, an ether, e.g., tetrahydrofuran and the like. Elevated temperatures may be suitable to enhance the rate of the reaction.

The compounds of formula (I) wherein L is a radical of formula (b-3) wherein $Z^2$ is a direct bond and $Z^1$ is other than a direct bond, said compounds being represented by (I-c-9), can be prepared by reacting a reagent of formula (XVI) or a functional derivative thereof with a compound of formula (I-c-8)

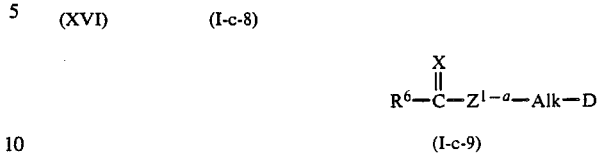

The reaction of (XVI) with (I-c-8) may generally be conducted following art-known esterification- or amidation reaction procedures. For example, the carboxylic acid may be converted into a reactive derivative, e.g., an anhydride or a carboxylic acid halide, which subsequently, is reacted with (I-c-8); or by reacting (XVI) and (I-c-8) with a suitable reagent capable of forming amides or esters, e.g., dichclohexylcarbodiimide, 2-chloro-1-methylpyridinium iodide and the like. Said reactions are most conveniently conducted in a suitable solvent such as, for example, an ether, e.g., tetrahydrofuran, a halogenated hydrocarbon, e.g., dichloromethane, trichloromethane or a polar aprotic solvent. The addition of a base such as N,N-diethylethanamine may be appropriate.

The compounds of formula (I) wherein L is a radical of formula $L^3$—$C_{2-6}$alkanediyl, said $L^3$ being $Ar^2$, Het, $Ar^2$-sulfonyl or a radical of formula $R^6$—$Z^2$—C(=X)—, and said compounds being represented by formula (I-c-10), may also be prepared by reacting an appropriate alkenylene of formula (XVII) with a compound of formula (I-d).

$L^3$—$C_{2-6}$alkenediyl-H + H—D ⟶ $L^3$—$C_{2-6}$alkanediyl—D (XVII)        (I-d)         (I-c-10)

The compounds of formula (I) wherein L is a radical of formula (b-4) or a 2-hydroxyethyl, said compounds being represented by formula (I-c-11), may also be prepared by reacting a reagent (XVIII) with a compound of formula (I-d).

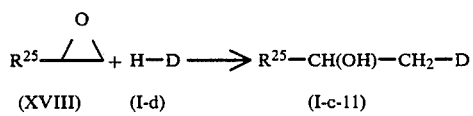

(XVIII)   (I-d)        (I-c-11)

$R^{25}$ in (XVIII) and (I-c-11) being hydrogen or a radical $R^7$—O—$CH_2$—. The reactions of (XVII) with (I-d) and (XVIII) with (I-d) may be conducted by stirring and, if desired, heating the reactants. The said reactions may be conducted in a suitable solvent such as, for example, a ketone, e.g., 2-propanone, 4-methyl-2-pentanone, an ether, e.g., tetrahydrofuran, 1,1'-oxybisethane, an alcohol, e.g., methanol, ethanol, 1-butanol, a polar aprotic solvent, e.g., N,N-dimethylformamide, N,N-dimethylacetamide, and the like.

The compounds of formula (I) wherein $R^4$, $R^5$ or $R^6$ are Het, may also be prepared following procedures for preparing ring systems which are known in the art or analogues procedures thereof. A number of such cyclization procedures are described in for example, the Published European Patent Publication No. 151,826, incorporated herein as reference.

For example, compounds of formula (I-c-12) can be obtained by a cyclodesulfurization reaction of (I-c-13) following similar procedures as described for the preparation of (I-b-1) from (VII).

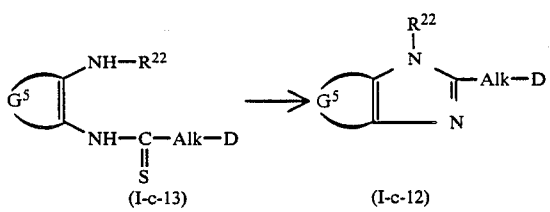

(I-c-13)    (I-c-12)

In (I-c-13) and (I-c-12) $G^5$ and $R^{22}$ have the same meanings as described hereinabove.

The compounds of formula (I) can also be converted into each other following art-known procedures of functional grouptransformation. Some examples of such procedures will be cited hereinafter.

The compounds of formula (I), wherein —B— is —S— may be converted into the corresponding compounds of formula (I), wherein —B— is —SO— or —SO$_2$— by an appropriate oxidation reaction, e.g., by reacting the former compounds with a suitable oxidating agent such as, for example, potassium periodate, a peroxide, e.g., 3-chlorobenzenecarboperoxoic acid, hydrogen peroxide, and the like, in a suitable solvent such as, for example, an ether, e.g., tetrahydrofuran, 1,1'-oxybisethane, a hydrocarbon, e.g., benzene, a halogenated hydrocarbon, e.g., dichloromethane, trichloromethane and the like. In the instance where a sulfinyl is desired, said oxidation reaction is preferably conducted at lower temperatures with approximately one equivalent of the oxidating agent, while where a sulfonyl is desired, said oxidation reaction may be conducted at room or at an elevated temperature with an excess of oxidating agent.

The compounds of formula (I) containing a cyano substituent can be converted into the corresponding amines by stirring and, if desired, heating the starting cyano compounds in a hydrogen containing medium in the presence of a suitable amount of an appropriate catalyst such as, for example, platinum-on-charcoal, Raney-nickel and the like catalyst. Suitable solvents are, for example, methanol, ethanol and the like.

The hydrogen atom of the amino function(s) of compounds of formula (I) may be substituted following art-known procedures such as, for example, N-alkylation, N-acylation, reductive N-alkylation and the like methods. For example alkylcarbonyl, arylcarbonyl and the like groups may be introduced by reacting the starting amine with an appropriate carboxylic acid or a derivative thereof such as, for example, an acid halide, acid anhydride and the like.

The compounds of formula (I) containing a substituted amine may be converted into the corresponding compounds of formula (I) wherein said nitrogen bears a hydrogen atom following art-known methods for preparing NH group. For example, where said amine is substituted with a C$_{1-6}$alkyloxycarbonyl group by treating the starting material with an acid or a base in a suitable solvent. As suitable acids or bases there may be cited hydrohalic acids, e.g., hydrochloric acid or hydrobromic acid, sulfuric, phosphoric and the like acids preferably employed as an aqueous solution or mixed with, e.g., acetic acid. Suitable bases are the alkali metal hydroxides, hydrides or alkoxides in an aqueous or alcoholic medium. Or, where said nitrogen is substituted with an Ar$^2$—CH$_2$ group, by treating the starting compounds with hydrogen in the presence of a suitable catalyst, e.g., palladium-on-charcoal, platinum-on-charcoal, preferably in an alcoholic medium and the like.

The compounds of formula (I) containing a nitrogen atom substituted with Ar$^2$—CH$_2$— may also be converted into the corresponding compounds where said nitrogen is substituted with C$_{1-6}$alkyloxycarbonyl, for example by treating the former compounds with a C$_{1-6}$alkylcarbonohalidate, e.g., ethyl carbonochloridate in the presence of a suitable solvent, e.g., methylbenzene and, if desired, in the presence of an appropriate base.

The compounds of formula (I) wherein the piperidine, pyrrolidine or hexahydro-1H-azepine nitrogen is substituted with a C$_{1-6}$alkyloxycarbonyl group may be converted into the corresponding compounds wherein the ring nitrogen is substituted with methyl by reducing the starting compounds with an appropriate reductant such as, likewise tetrahydroaluminate.

The compounds of formula (I) containing an amino group may be converted into the corresponding isothiocyanato containing compounds by treating the starting amino compounds with CS$_2$ optionally in the presence of N,N-methanetetraylbis[cyclohexamine].

Compounds of formula (I) containing a hydroxy substituent, such as those compounds of formula (I) wherein —G—R$^1$ is hydroxy, may further be O-alkylated with an appropriate reagent in the presence of a suitable base. Suitable bases are alkali metal hydrides, such as sodium hydride.

The compounds of formula (I) containing an ester group may be converted into the corresponding carboxylic acids following art-known saponification procedures, e.g., by treating the starting compound with an aqueous alkaline or an aqueous acidic solution. Vice versa, the carboxylic acid group may be converted into the corresponding ester group following art-known esterification procedures.

In all of the foregoing and in the following preparations, the reaction products may be isolated from the reaction mixture and, if necessary, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid, e.g., hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may also be converted to their therapeutically active non-toxic metal or amine substitution salt forms by treatment with appropriate organic or inorganic bases.

Some intermediates and starting materials in the foregoing preparations are known compounds which may be prepared according to art-known methodologies of preparing said or similar compounds and others are new. A number of such preparation methods will be described hereinafter in more detail.

The intermediates of formula (II), wherein B is $CH_2$, $X^3$ is NH and W is $C_{1-6}$alkyloxy, said intermediates being represented by the formula (II-b), can be prepared by reacting a (cyanomethyl) derivative of formula (XIX) with an alcohol, e.g., methanol, ethanol and the like, in the presence of an acid, e.g., hydrochloric acid.

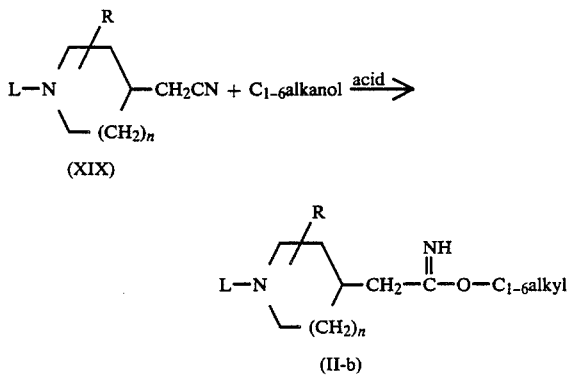

The intermediates of formula (IV) may be prepared by a reduction reaction of an appropriate 4-piperidinone, 3-pyrrolidinone or hexahydro-1H-azepin-4-one, and, if desired, followed by an appropriate art-known groupstransformation procedure, for example, in the instance where a compound of formula (IV-b) is desired, by reacting the thus obtained alcohol with thionyl chloride, methylsulfonyl chloride and the like in order to obtain an appropriate leaving group.

Starting materials such as intermediates of formulae (VIII), (X) and (XI) can conveniently be prepared following art-known procedures as described in, for example, U.S. Pat. Nos. 4,219,559; 4,335,127; 4,342,870; 4,443,451; 4,634,704; 4,695,569 and 4,588,722, which are incorporated herein as reference.

From formula (I) it is evident that the compounds of this invention may have several asymmetric carbon atoms in their structure. Each of these chiral centers may be present in a R- and a S-configuration, this R- and S-notation being in correspondence with the rules described by R. S. Cahn, C. Ingold and V. Prelog in Angew. Chem., Int. Ed. Engl., 5, 385, 511 (1966).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

Stereochemically isomeric forms of the compounds of formula (I) are naturally intended to be embraced within the scope of the invention.

The compounds of formula (I), the pharmaceutically acceptable acid-addition salts and possible stereochemically isomeric forms thereof possess useful pharmacological properties. More particularly, they are active as anti-histaminics which activity can clearly be demonstrated by, e.g., the results obtained in the "Protection of Rats from Compound 48/80-induced lethality"-test, the "Histamine antagonism in Guinea Pig"-test and the "Ascaris Allergy test in Dogs"-test described in Arch. Int. Pharmacodyn. Ther. 251, 39–51 (1981). Apart from their anti-histaminic properties some of the subject compounds also show serotonin-antagonism. Whereas some are active in the "Stress Ulcer Antagonism in Rats"-test which is related to the test described in European Journal of Pharmacology, 137 (1987) 127–129.

Furthermore the compounds of formula (I), the pharmaceutically acceptable acid-addition salts and stereochemically isomeric forms thereof are particularly attractive due to their favourable pharmacokinetical profile. In particularly, some show a rapid onset so that their anti-histaminic effects are almost instantaneously present.

In view of their anti-histaminic properties, the compounds of formula (I) and their acid-addition salts are very useful in the treatment of allergic diseases such as, for example, allergic rhinitis, allergic conjunctivities, chronic urticaria, allergic astma and the like.

In view of their useful pharmacological properties the subject compounds may be formulated into various pharmaceutical forms for administration purposes particularly in aqueous compositions as the compounds of formula (I) show an increased water solubility. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deletorious effect on the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention is also related with a method of treating allergic diseases in warm-blooded animals suffering from said allergic diseases by administering an effective anti-allergic amount of a compound of formula (I) or a pharmaceutically acceptable acid addition salt thereof.

Those of skill in treating allergic diseases in warm-blooded animals could easily determine the effective amount from the test results presented hereinafter. In general it is contemplated that an effective amount would be from 0.001 mg/kg to 100 mg/kg body weight, and more preferably from 0.01 mg/kg to 1 mg/kg body weight.

The following examples are intented to illustrate and not to limit the scope of the present invention in all its aspects. Unless otherwise stated all parts therein are by weight.

EXPERIMENTAL PART

A. Preparation of Intermediates

Example 1

2350 Parts of hydrogen chloride were bubbled through 5600 parts of cooled ethanol (ice bath) at 10° C. Then there were added dropwise, during a 45 minutes-period, 1500 parts of 1-(phenylmethyl)-4-piperidineacetonitrile. Upon completion, the whole was stirred for 20 hours at room temperature. The reaction mixture was evaporated and the residue was stirred in 2400 parts of acetonitrile. The product was filtered off, washed with 560 parts of acetonitrile and dried, yielding 2000 parts (85.7%) of O-ethyl 1-(phenylmethyl)-4-piperidineethanimidate dihydrochloride (interm. 1).

Example 2

(a) A mixture of 46 parts of ethyl hexahydro-4-oxo-1H-azepine-1-carboxylate, 26 parts of benzenemethanamine, 2 parts of a solution of thiophene in methanol 4% and 400 parts of methanol was hydrogenated at normal pressure and at room temperature with 4 parts of palladium-on-charcoal catalyst 10%. After the calculated amount of hydrogen was taken up, the catalyst was filtered off and the filtrate was evaporated, yielding 69.1 parts (100%) of ethyl hexahydro-4-[(phenylmethyl)amino]-1H-azepine-1-carboxylate as a residue (interm. 2).

(b) 69.1 Parts of ethyl hexahydro-4-[(phenylmethyl)amino]-1H-azepine-1-carboxylate were hydrogenated in the presence of a solution of thiophene in methanol 4% and methanol at normal pressure and at room temperature with 4 parts of palladium-on-charcoal catalyst 10%. After the calculated amount of hydrogen was taken up, the catalyst was filtered off and the filtrate was evaporated, yielding 46.9 parts (100%) of ethyl 4-aminohexahydro-1H-azepine-1-carboxylate as a residue (interm. 3).

(c) To a stirred and cooled (−10° C.) mixture of 63 parts of carbon disulfide, 52.1 parts of N,N'-methanetetraylbis[cyclohexanamine] and 360 parts of tetrahydrofuran were added dropwise 46.9 parts of ethyl 4-aminohexahydro-1H-azepine-1-carboxylate. Upon complete addition, the reaction mixture was stirred for 2 hours at room temperature. The reaction mixture was evaporated and the residue was stirred in 2,2'-oxybispropane. The precipitate was filtered off and the filtrate was evaporated, yielding 70.75 parts (100%) of ethyl hexahydro-4-isothiocyanato-1H-azepine-1-carboxylate as a residue (interm. 4).

Example 3

To a stirred and cooled mixture of 4 parts of sodium hydroxide in 60 parts of water were added successively 7.9 parts of carbon disulfide and 17.2 parts of ethyl 4-amino-1-piperidinecarboxylate at a temperature below 10° C. Stirring was continued for 30 minutes at this temperature. Then there were added dropwise 10.9 parts of ethyl carbonochloridate (exothermic reaction: temperature rises to about 35° C.). Upon completion, stirring was continued for 2 hours at 60° C. The reaction mixture was cooled and the product was extracted with methylbenzene. The extract was dried, filtered and evaporated, yielding 22 part (100%) of ethyl 4-isothiocyanato-1-piperidinecarboxylate as a residue (interm. 5).

In a similar manner there were also prepared: 4-isothiocyanato-1-(phenylmethyl)piperidine as a residue (interm. 6) and ethyl 3-isothiocyanato-1-pyrrolidinecarboxylate as a residue (interm. 7).

Example 4

(a) A mixture of 19 parts of 2-chloro-3-nitropyridine, 13.5 parts of 2-ethoxyethanamine, 13 parts of sodium hydrogen carbonate and 240 parts of ethanol was stirred for 6 hours at reflux temperature. After cooling, the mixture was filtered over diatomaceous earth and the filtrate was evaporated, yielding 25.5 parts (100%) of N-(2-ethoxyethyl)-3-nitro-2-pyridinamine as a residue (interm. 8).

(b) A mixture of 25.5 parts of N-(2-ethoxyethyl)-3-nitro-2-pyridinamine, 2 parts of a solution of thiophene in methanol 4% and 200 parts of methanol was hydrogenated at normal pressure and at 50° C. with 3 parts of palladium-on-charcoal catalyst 10%. After the calculated amount of hydrogen was taken up, the catalyst was filtered off and the filtrate was evaporated, yielding 25 parts (100%) of $N^2$-(2-ethoxyethyl)-2,3-pyridinediamine as a residue (interm. 9).

(c) A mixture of 25 parts of $N^2$-(2-ethoxyethyl)-2,3-pyridinediamine, 43 parts of ethyl 4-isothiocyanato-1-piperidinecarboxylate and 450 parts of tetrahydrofuran was stirred overnight at reflux temperature. The reaction mixture was evaporated and the residue was taken up in trichloromethane. The organic layer was washed twice with water, dried, filtered and evaporated. The residue was crystallized from a mixture of acetonitrile and 2,2'-oxybispropane. The product was filtered off and dried, yielding 35 parts (73.7%) of ethyl 4-[[[[2-[(2-ethoxyethyl)amino]-3-pyridinyl]amino]thioxomethyl]amino]-1-piperidinecarboxylate as a residue (interm. 10).

In a similar manner there were also prepared:

(b) A mixture of 44 parts of N-(2-amino-5-methoxyphenyl)-N'-(1-methyl-4-piperidinyl)thiourea, 38.9 parts of mercury(II) oxide and 270 parts of tetrahydrofuran was stirred and refluxed for 2 hours at reflux temperature. The reaction mixture was filtered while hot over diatomaceous earth and the filtrate was evaporated. The residue was purified by column chromatography over silica gel first using a mixture of trichloromethane and methanol (95:5 by volume) and then a mixture of

TABLE

| int. | L | n | G | R | $R^1$ | $A^1=A^2-A^3=A^4$ | Physical data |
|---|---|---|---|---|---|---|---|
| 11 | $CH_3-CH_2-O-CO-$ | 1 | O | — | —H | $-N=CH-CH=CH-$ | mp. 154° C. |
| 12 | $CH_3-CH_2-O-CO-$ | 1 | S | — | $-CH_2-\text{(furan)}$ | $-N=CH-CH=CH-$ | residue |
| 13 | $CH_3-CH_2-O-CO-$ | 1 | O | — | $-CH_2-\text{(furan)}$ | $-N=CH-CH=CH-$ | residue |
| 14 | $CH_3-CH_2-O-CO-$ | 1 | O | — | $-CH_2-CH_2OH$ | $-N=CH-CH=CH-$ | residue |
| 15 | $C_6H_5-CH_2-$ | 1 | O | — | $-CH_2-CH_2OH$ | $-CH=CH-CH=CH-$ | residue |
| 16 | $C_6H_5-CH_2-$ | 1 | NH | — | $-COO-CH_2-CH_3$ | $-N=CH-CH=CH-$ | residue |
| 17 | $CH_3-CH_2-O-CO-$ | 1 | O | — | $-CH_2-CH_3$ | $-CH=CH-N=CH-$ | residue |
| 18 | $C_6H_5-CH_2-$ | 1 | O | — | $-CH_2-CH_3$ | $-N=CH-N=CH-$ | residue |
| 19 | $CH_3-CH_2-O-CO-$ | 1 | O | — | $-CH_2-CH_3$ | $-CH=N-CH=CH-$ | residue |
| 20 | $CH_3-CH_2-O-CO-$ | 0 | O | — | $-CH_2-CH_3$ | $-N=CH-CH=CH-$ | residue |
| 21 | $CH_3-CH_2-O-CO-$ | 2 | O | — | —H | $-CH=CH-CH=CH-$ | residue |
| 22 | $CH_3-$ | 1 | O | — | $-CH_2-CH_3$ | $-CH=CH-C(CH_3)=CH-$ | residue |
| 23 | $CH_3-CH_2-O-CO-$ | 2 | O | — | $-CH_2-CH_3$ | $-N=CH-CH=CH-$ | residue |
| 25 | $CH_3-OCO-$ | 1 | NH | 3-$CH_3$ | $-CH_2-CH_3$ | $-N=CH-CH=CH-$ | residue cis + trans | and ethyl 4-[[[[2-[[2-(diethylamino)ethyl]amino]-3-pyridinyl]amino]thioxomethyl]amino]-1-piperidinecarboxylate as a residue (interm. 24).

Example 5

(a) A mixture of 37.5 parts of 4-isothiocyanato-1-methylpiperidine, 21.8 parts of 4-methoxy-1,2-benzenediamine and 270 parts of tetrahydrofuran was stirred and refluxed for 2 hours. The whole was evaporated, yielding 44 parts (100%) of N-(2-amino-5-methoxyphenyl)-N'-(1-methyl-4-piperidinyl)thiourea as a residue (interm. 26).

trichloromethane and methanol, saturated with ammonia, (85:15 by volume) as eluents. The pure fractions were collected and the eluent was evaporated, yielding 50.5 parts (100%) of 5-methoxy-N-(1-methyl-4-piperidinyl)-1H-benzimidazol-2-amine as a residue (interm. 27).

In a similar manner there was also prepared: 5,6-dimethoxy-N-(1-methyl-4-piperidinyl)-1H-benzimidazol-2-amine (interm. 28).

Example 6

A mixture of 32 parts of 1-chloro-2-ethoxyethane, 94.5 parts of N-(4-piperidinyl)-1H-benzimidazol-2-amine dihydrobromide, 90 parts of sodium carbonate and 540 parts of N,N-dimethylacetamide was stirred overnight at 70° C. After cooling, the reaction mixture was poured into water. The product was extracted with dichloromethane. The extract was dried, filtered and evaporated. The residue was boiled in acetonitrile. After cooling, the precipitated product was filtered off and dried, yielding 42.4 parts (58.8%) of N-[1-(2-ethoxyethyl)-4-piperidinyl]-1H-benzimidazol-2-amine; mp. 212° C. (interm. 29).

Example 7

A mixture of 36.6 parts of N-(4-piperidinyl)-1H-benzimidazol-2-amine dihydrobromide, 10 parts of poly(oxymethylene), 2 parts of a solution of thiophene in methanol 4%, 200 parts of methanol and 20 parts of potassium hydroxide was hydrogenated at normal pressure and at room temperature with 4 parts of palladium-on-charcoal catalyst 10%. After the calculated amount of hydrogen was taken up, the catalyst was filtered off and the filtrate was evaporated. The residue was treated with a sodium hydroxide solution. The precipitated product was filtered off and dried, yielding 13.7 parts (59.4%) of N-(1-methyl-4-piperidinyl)-1H-benzimidazol-2-amine (interm 30).

Example 8

To a stirred dispersion of 28.9 parts of ethyl 4-(1H-benzimidazol-2-ylamino)-1-piperidinecarboxylate in 282 parts of N,N-dimethylformamide were added 4.8 parts of a sodium hydride dispersion 50% under nitrogen atmosphere (gas evolution—slightly exothermic reaction). The mixture was stirred for 1.5 hour at room temperature. 8.3 Parts of chloroacetonitrile were added dropwise at ±10° C. while cooling in an ice bath. Upon complete addition, the temperature was allowed to reach room temperature and then stirred overnight. The reaction mixture was evaporated and the residue was taken up in water and 4-methyl-2-pentanone. The separated organic layer was washed three times with water, dried, filtered and evaporated. The residue was purified by column chromatography over silica gel using a mixture of trichloromethane and methanol (95:5 by volume) as eluent. The pure fractions were collected and the eluent was evaporated. The residue was crystallized from methylbenzene. The product was filtered off and dried, yielding 12.4 parts (37.8%) of ethyl 4-[[1-(cyanomethyl)-1H-benzimidazol-1-yl]amino]-1-piperidinecarboxylate as a residue (interm. 31).

B. Preparation of Final Compounds

Example 9

A mixture of 9 parts of ethyl 4-[[[[2-[(2-ethoxyethyl)amino]-3-pyridinyl]amino]thioxomethyl]amino]-1piperidinecarboxylate, 13 parts of mercury(II) oxide, 0.1 parts of sulfur and 120 parts of ethanol was stirred for 2 hours at reflux temperature. The reaction mixture was filtered over diatomaceous earth and the filtrate was evaporated. The residue was converted into the hydrochloride salt in 2-propanone. The salt was filtered off and dried, yielding 6.5 parts (71.0%) of ethyl 4-[[3-(2-ethoxyethyl)-3H-imidazo[4,5-b]pyridin-2-yl]amino]-1-piperidinecarboxylate monohydrochloride; mp. 185.0° C. (compound 1).

In a similar manner there were also prepared:

TABLE

| Comp. No. | L | n | G | R¹ | A¹ | Physical data |
|---|---|---|---|---|---|---|
| 2 | CH₃—CH₂—O—CO— | 1 | O | —H | N | residue |
| 3 | CH₃—CH₂—O—CO— | 1 | S |  | N | residue |
| 4 | CH₃—CH₂—O—CO— | 1 | O | 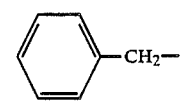 | N | residue |
| 5 | CH₃—CH₂—O—CO— | 1 | O | —CH₂—CH₂—OH | N | residue |
| 6 | benzyl —CH₂— | 1 | O | —CH₂—CH₂—OH | CH | residue |
| 7 | CH₃—CH₂—O—CO— | 2 | O | —CH₂—CH₃ | CH | residue |
| 8 | CH₃—CH₂—O—CO— | 0 | O | —CH₂—CH₃ | N | residue |
| 9 | CH₃—CH₂—O—CO— | 2 | O | —H | CH | residue | and ethyl 4-[[3-[2-(diethylamino)ethyl]-3H-imidazo[4,5-b]pyridin-2-yl]amino]-1-piperidinecarboxylate as a residue (compound 10).

Example 10

A mixture of 22.4 parts of N-[4-[(2-ethoxyethyl)amino]-5-pyrimidinyl]-N'-[1-(phenylmethyl)-4-piperidinyl]thiourea, 17.3 parts of mercury(II) oxide, 0.1 parts of sulfur and 270 parts of tetrahydrofuran was stirred for 2 hours at reflux temperature. The reaction mixture was filtered while hot over diatomaceous earth. The filtrate was evaporated and the residue was purified by column chromatography over silica gel using a mixture of trichloromethane and methanol (95:5 by volume) as eluent. The pure fractions were collected and the eluent was evaporated, yielding 16.3 parts (79.3%) of 9-(2-ethoxyethyl)-N-[1-(phenylmethyl)-4-piperidinyl]-9H-purin-8-amine as a residue (compound 11).

In a similar manner there were also prepared:
ethyl 4-[[1-(2-ethoxyethyl)-1H-imidazo[4,5-c]pyridin-2-yl]amino]-1-piperidinecarboxylate as a residue (compound 12);
ethyl 4-[[3-(2-ethoxyethyl)-3H-imidazo[4,5-c]pyridine-2-yl]amino]-1-piperidinecarboxylate as a residue (compound 13);
ethyl 4-[[3-[(2-ethoxyethyl)-3H-imidazo[4,5-b]pyridin-2-yl]amino]hexahydro-1H-azepine-1-carboxylate as a residue (compound 14) and
methyl (cis+trans)-4-[[3-(2-ethoxyethyl)-3H-imidazo[4,5-b]pyridin-2-yl]amino]-3-methyl-1-piperidinecarboxylate as a residue (compound 15).

Example 11

A mixture of 13 parts of N-[2-[(2-ethoxyethyl)amino]-5-methylphenyl]-N$^1$-(1-methyl-4-piperidinyl)thiourea, 8.8 parts of mercury(II) oxide and 90 parts of tetrahydrofuran was stirred for 1 hour at reflux temperature. The reaction mixture was filtered while hot over diatomaceous earth and the filtrate was evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the (E)-2-butenedioate salt in ethanol. The salt was filtered off and dried, yielding 6.2 parts (30.5%) of 1-(2-ethoxyethyl)-5-methyl-N-(1-methyl-4-piperidinyl)-1H-benzimidazol-2-amine (E)-2-butenedioate(1:2); mp. 218.4° C. (compound 16).

Example 12

A mixture of 120 parts of O-ethyl 1-(phenylmethyl)-4-piperidineethanimidate dihydrochloride, 45.9 parts of 2-(2,3-diamino-2-pyridinyl)ethanol and 400 parts of methanol was stirred overnight at reflux temperature. Another portion of 60 parts of O-ethyl 1-(phenylmethyl)-4-piperidineethanimidate dihydrochloride was added and stirring was continued for 8 hours at reflux. After cooling, the reaction mixture was evaporated and the residue was taken up in water. The aqueous layer was treated with an ammonium hydroxide solution and the product was extracted with dichloromethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated, yielding 87 parts (82.7%) of 2-[[1-(phenylmethyl)-4-piperidinyl]methyl]-3H-imidazo[4,5-b]pyridine-3-ethanol as a residue (compound 17).

In a similar manner there was also prepared:
3-(2-ethoxyethyl)-2-[[1-(phenylmethyl)-4-piperidinyl]methyl]-3H-imidazo[4,5-b]pyridine as a residue (compound 18).

Example 13

To a stirred mixture of 34.64 parts of ethyl 4-hydroxy-1-piperidinecarboxylate and 940 parts of N,N-dimethylformamide were added portionwise 10 parts of a sodium hydride dispersion 50% at room temperature under nitrogen atmosphere. Upon complete addition, stirring was continued for 1 hour at room temperature. A solution of 45 parts of 2-chloro-1-(2-ethoxyethyl)-1H-benzimidazole in N,N-dimethylformamide was added dropwise at 50° C. Upon completion, the whole was stirred overnight at 50° C. The reaction mixture was poured into ice water and the product was extracted with trichloromethane. The extract was dried, filtered and evaporated, yielding 50 parts (69.1%) of ethyl 4-[[1-(2-ethoxyethyl)-1H-benzimidazol-2-yl]oxy]-1-piperidinecarboxylate as a residue (compound 19).

Example 14

A mixture of 14 parts of ethyl 4-[[3-(2-hydroxyethyl)-3H-imidazo[4,5-b]pyridin-2-yl]amino]-1-piperidinecarboxylate, 22 parts of potassium hydroxide and 160 parts of 2-propanol was stirred overnight at reflux temperature. The reaction mixture was evaporated and the residue was taken up in water. The aqueous layer was salted out with potassium carbonate and the product was extracted with tetrahydrofuran. The extract was dried, filtered and evaporated. The residue was crystallized from acetonitrile. The product was filtered off and dried, yielding 5.5 parts (52.3%) of 2-(4-piperidinylamino)-3H-imidazo[4,5-b]pyridine-3-ethanol; mp. 156.9° C. (compound 20).

In a similar manner there were also prepared:

TABLE

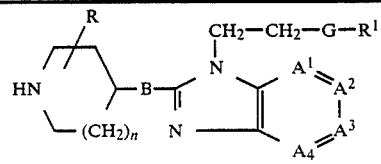

| Comp. No. | n | B | G | R | R$^1$ | A$^1$=A$^2$—A$^3$=A$^4$ | Physical data |
|---|---|---|---|---|---|---|---|
| 21 | 1 | NH | O | — | —CH$_2$—CH$_3$ | —N=CH—CH=CH— | 2(COOH)$_2$/mp. 208.5° C. |
| 22 | 1 | NH | S | — | —CH$_2$ (furyl) | —N=CH—CH=CH— | 2(COOH)$_2$/mp. 193.0° C. |

TABLE -continued

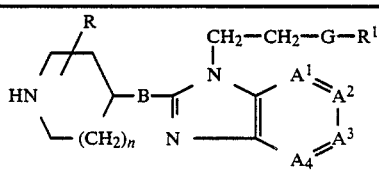

| Comp. No. | n | B | G | R | R¹ | A¹=A²—A³=A⁴ | Physical data |
|---|---|---|---|---|---|---|---|
| 23 | 1 | NH | O | — | -CH₂-(furan) | —N=CH—CH=CH— | 2HCl/mp. 265.2° C.(dec.) |
| 24 | 1 | NH | O | — | —CH₂—CH₂—OH | —N=CH—CH=CH— | *(1:2)/H₂O/mp. 155.2° C. |
| 25 | 1 | O | O | — | —CH₂—CH₃ | —CH=CH—CH=CH— | 2HCl/mp. 131.9° C. |
| 26 | 1 | NH | O | — | —CH₂—CH₃ | —CH=CH—N=CH— | mp. 148.5° C. |
| 27 | 1 | NH | O | — | —CH₂—CH₃ | —CH=N=CH—CH— | residue |
| 28 | 1 | CH₂ | O | — | —CH₂—CH=CH₂ | —N=CH—CH=CH— | *(2:3)/mp. 171.9° C. |
| 29 | 0 | NH | O | — | —CH₂—CH₃ | —N=CH—CH=CH— | 2(COOH)₂/mp. 156.8° C. |
| 30 | 1 | NH | O | 3-CH₃ | —CH₂—CH₃ | —N=CH—CH=CH— | *(2:3)/cis/mp. 190.7° C. |
| 31 | 1 | NH | O | 3-CH₃ | —CH₂—CH₃ | —N=CH—CH=CH— | *(1:2)/ethanol/ cis + trans/mp. 181.0° C. |

* = (E)-2-butenedioate and N,N-dimethyl-2-(4-piperidinylamino-1H-benzimidazole-1-ethanamine; mp. 126.5° C. (compound 32);

N,N-diethyl-2-(4-piperidinylamino)-3H-imidazo[4,5-b]pyridine-3-ethanamine (E)-2-butenedioate(1:3); mp. 180.8° C. (compound 33) and 1-[(2-methoxyethoxy)methyl)]-N-(4-piperidinyl)-1H-benzimidazol-2-amine; mp. 148.5° C. (compound 34).

Example 15

A mixture of 27 parts of ethyl hexahydro-4-[[1-[2-(2-pyrimidinyloxy)ethyl]-1H-benzimidazol-2-yl]amino]-1H-azepine-1-carboxylate, 160 parts of 1-butanol, 28 parts of potassium hydroxide and 2 parts of water was stirred overnight at reflux temperature. The reaction mixture was diluted with water and the whole was extracted with 1-butanol. The extract was dried, filtered and evaporated. The residue was taken up in water and the product was extracted with dichloromethane. The extract was dried, filtered and evaporated. The residue was converted into the (E)-2-butenedioate salt in ethanol. The salt was filtered off and dried, yielding 9.77 parts (38.5%) of 2-[(hexahydro-1H-azepin-4-yl)amino]-1H-benzimidazole-1-ethanol (E)-2-butenedioate(1:2); mp. 176.1° C. (compound 35).

In a similar manner there was also prepared:
3-(2-ethoxyethyl)-N-(hexahydro-1H-azepin-4-yl)-3H-imidazo[4,5-b]pyridin-2-amine (E)-2-butenedioate(2:3); mp. 180.0° C. (compound 36).

Example 16

A mixture of 105 parts of ethyl 4-[[1-(2-ethoxyethyl)-1H-benzimidazol-2-yl]amino]hexahydro-1H-azepine-1-carboxylate, 79 parts of potassium hydroxide and 833 parts of 1,2-ethanediol was stirred overnight at reflux temperature. The reaction mixture was distilled in vacuo and the residue was taken up in dichloromethane. The organic phase was filtered and the filtrate was evaporated. The residue was purified by column chromatography over silica gel using a mixture of trichloromethane and methanol (90:10 by volume) as eluent. The pure fractions were collected and the eluent was evaporated. The residue was converted into the ethanedioate salt. The salt was filtered off and crystallized from 2-propanol. The product was filtered off and dried, yielding 16.4 parts (9.9%) of 1-(2-ethoxyethyl)-N-(hexahydro-1H-azepin-4-yl)-1H-benzimidazol-2-amine ethanedioate(1:3), monohydrate (compound 37).

Example 17

A mixture of 140 parts of 2-[2-[2-[[1-(phenylmethyl)-4-piperidinyl]amino]-1H-benzimidazol-1-yl]ethoxy]ethanol and 480 parts of methanol was hydrogenated at normal pressure and at room temperature with 5 parts of palladium-on-charcoal catalyst 10%. After the calculated amount of hydrogen was taken up, the catalyst was filtered off over diatomaceous earth and the filtrate was evaporated. The residue was crystallized twice from acetonitrile. The product was filtered off and dried, yielding 53.3 parts (46.0%) of 2-[2-[2-(4-piperidinylamino)-1H-benzimidazol-1-yl]ethoxy]ethanol; mp. 163.7° C. (compound 38).

In a similar manner there were also prepared:
3-(2-ethoxyethyl)-2-(4-piperidinylmethyl)-3H-imidazo[4,5-b]pyridine (E)-2-butenedioate(2:3); mp. 177.9° C. (compound 39);

ethyl H-[2-[2-(4-piperidinylamino)-3H-imidazo[4,5-b]pyridin-3-yl]ethyl]glycine ethanedioate(1:3), dihydrate; mp. 187.8° C. (compound 40) and N-ethyl-N-[2-[2-(4-piperidinylamino)-3H-imidazo[4,5-b]pyridin-1-yl]ethyl]acetamide; mp. 156.7° C. (compound 41).

Example 18

A mixture of 16.3 parts of 9-(2-ethoxyethyl)-N-[1-(phenylmethyl)-4-piperidinyl]-9H-purin-8-amine and 200 parts of methanol was hydrogenated at normal pressure and at room temperature with 4 parts of palladium-on-charcoal catalyst 10% and 6 parts of Raney nickel catalyst. After the calculated amount of hydrogen was taken up, the catalyst was filtered off and the filtrate was evaporated. The residue was purified by column chromatography over silica gel using a mixture of trichloromethane and methanol, saturated with ammonia, (90:10 by volume) as eluent. The first fraction was collected and the eluent was evaporated. The residue was converted into the (E)-2-butenedioate salt in methanol. The salt was filtered off and dried, yielding 1.98 parts (8.6%) of 9-(2-ethoxyethyl)-N-(4-piperidinyl)-9H-purin-8-amine (E)-2-butenedioate(1:2), hemihydrate; mp. 192.8° C. (compound 42).

Example 19

To a stirred and refluxed mixture of 13.5 parts of 2-[[1-(phenylmethyl)-4-piperidinyl]methyl]-3-[2-(2-propenyloxy)ethyl]-3H-imidazo[4,5-b]-pyridine and 90 parts of methylbenzene were added dropwise 5.4 parts of ethyl carbonochloridate. Upon complete addition, stirring was continued for 1 hour at reflux temperature. After cooling, the reaction mixture was diluted with water and the whole was treated with potassium carbonate. The product was extracted with methylbenzene. The extract was dried, filtered and evaporated, yielding 14 parts (75.1%) of ethyl 4-[[3-[2-(2-propenyloxy)ethyl]-3H-imidazo[4,5-b]pyridine-2-yl]methyl]-1-piperidinecarboxylate as a residue (compound 43).

Example 20

A mixture of 1.08 parts of 1-chloro-2-ethoxyethane, 2.9 parts of 3-(2-ethoxyethyl)-N-(4-piperidinyl)-3H-imidazo[4,5-b]pyridin-2-amine, 1.06 parts of sodium carbonate and 45 parts of N,N-dimethylacetamide was stirred overnight at 70° C. The reaction mixture was poured into water and the product was extracted with 4-methyl-2-pentanone. The extract was dried, filtered and evaporated. The residue was purified by filtration over silica gel using a mixture of trichloromethane and methanol (96:4 by volume) as eluent. The pure fractions were collected and the eluent was evaporated. The residue was converted into the ethanedioate salt in methanol. The salt was filtered off and dried, yielding 0.7 parts (12.9%) of 3-(2-ethoxyethyl)-N-[1-(2-ethoxyethyl)-4-piperidinyl]-3H-imidazo[4,5-b]pyridin-2-amine ethanedioate(1:2); mp. 176.1° C. (compound 44).

In a similar manner there were also prepared:

TABLE

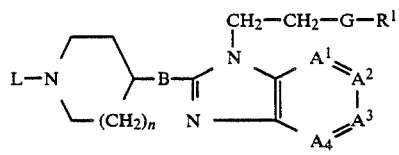

| Comp. No. | L | n | B | G | $R^1$ | $A^1=A^2-A^3=A^4$ | Physical data |
|---|---|---|---|---|---|---|---|
| 45 | CH$_3$—O—⟨phenyl⟩—CH$_2$—CH$_2$— | 1 | NH | O | —CH$_2$—CH$_3$ | —N=CH—CH=CH— | mp. 116.4° C. |
| 46 | ⟨pyrido-pyrazinone with CH$_3$⟩—CH$_2$—CH$_2$— | 1 | NH | O | —CH$_2$—CH$_3$ | —N=CH—CH=CH— | mp. 134.4° C. |
| 47 | CH$_3$—O—⟨phenyl⟩—CH$_2$—CH$_2$— | 1 | NH | O | —H | —N=CH—CH=CH— | mp. 132.3° C. |
| 48 | CH$_3$—CH$_2$—O—CH$_2$—CH$_2$— | 1 | NH | O | —H | —N=CH—CH=CH— | 2(COOH)$_2$/ mp. 189.9° C. |
| 49 | CH$_3$—CH$_2$—O—CH$_2$—CH$_2$— | 1 | NH | O | —CH$_2$—⟨furyl⟩ | —N=CH—CH=CH— | 2(COOH)$_2$/ mp. 182.5° C. |
| 50 | CH$_3$—O—⟨phenyl⟩—CH$_2$—CH$_2$— | 1 | NH | O | —CH$_2$—⟨furyl⟩ | —N=CH—CH=CH— | 2HCl/ mp. 265.1° C. |
| 51 | ⟨pyrido-pyrazinone with CH$_3$⟩—CH$_2$—CH$_2$— | 1 | NH | O | —CH$_2$—⟨furyl⟩ | —N=CH—CH=CH— | mp. 142.9° C. |

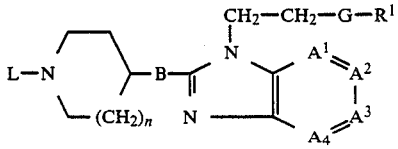

| Comp. No. | L | n | B | G | R¹ | A¹=A²—A³=A⁴ | Physical data |
|---|---|---|---|---|---|---|---|
| 52 | 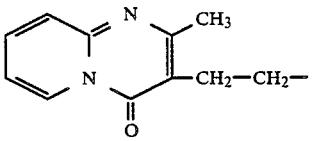 | 1 | NH | S | —CH₂—<furan> | —N=CH—CH=CH— | mp. 183.1° C. |
| 53 | CH₃—O—<phenyl>—CH₂—CH₂— | 1 | NH | S | —CH₂—<furan> | —N=CH—CH=CH— | mp. 116.5° C. |
| 54 | CH₃—O—<phenyl>—CH₂—CH₂— | 1 | NH | O | —CH₂—CH₂OH | —N=CH—CH=CH— | ½H₂O/ mp. 90.9° C. |
| 55 |  | 1 | NH | O | —CH₂—CH₂OH | —N=CH—CH=CH— | mp. 169.8° C. |
| 56 | CH₃—O—<phenyl>—CH₂—CH₂— | 1 | O | O | —CH₂—CH₃ | —CH=CH—CH=CH— | 2HCl/H₂O/ mp. 130.1° C. |
| 57 | CH₃—O—<phenyl>—CH₂—CH₂— | 1 | NH | O | —CH₂—CH₂OH | —CH=CH—CH=CH— | 2(COOH)₂/½H₂O mp. 197.0° C. |
| 58 | 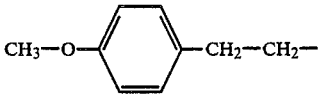 | 1 | NH | O | —CH₂—CH₂OH | —CH=CH—CH=CH— | mp. 185.7° C. |
| 59 | CH₃—O—<phenyl>—CH₂—CH₂— | 1 | CH₂ | O | —CH₂—CH₃ | —N=CH—CH=CH— | 1.5(COOH)₂ mp. 143.8° C. |
| 60 |  | 1 | NH | O | —CH₂—CH₃ | —CH=CH—N=CH— | *(1:2)/2H₂O mp. 180.0° C. |
| 61 | CH₃—C(=O)—CH₂—CH₂—CH₂— | 1 | NH | O | —CH₂—CH₃ | —N=CH—CH=CH— | 2(COOH)₂/ mp. 182.4° C. |
| 62 |  | 1 | CH₂ | O | —CH₂—CH₃ | —N=CH—CH=CH— | 3HCl/3H₂O mp. 196.5° C. |

TABLE -continued

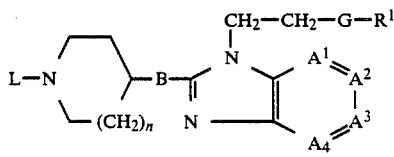

| Comp. No. | L | n | B | G | R¹ | A¹=A²—A³=A⁴ | Physical data |
|---|---|---|---|---|---|---|---|
| 63 | 4-F-C₆H₄-O-(CH₂)₃- | 1 | NH | O | -CH₂-CH₃ | -N=CH-CH=CH- | mp. 108.8° C. |
| 64 | (thiazoline-pyrimidinone substituent)-CH₂-CH₂- | 1 | NH | O | -CH₂-CH₃ | -N=CH-CH=CH- | mp. 152.1° C. |
| 65 | 4-F-C₆H₄-C(O)-(CH₂)₃- | 1 | NH | O | -CH₂-CH₃ | -N=CH-CH=CH- | 2(COOH)₂/ mp. 185.4° C. |
| 66 | (pyrido-pyrimidinone substituent)-CH₂-CH₂- | 1 | NH | O | -CH₂-CH₃ | -CH=N-CH=CH- | *(2:5)/2.5H₂O mp. 179.8° C. |
| 67 | (thiazole substituent)-CH₂-CH₂- | 1 | NH | O | -CH₂-CH₃ | -N=CH-CH=CH- | 2(COOH)₂/ mp. 240.4° C. |
| 68 | (quinazolinedione substituent)-CH₂-CH₂- | 1 | NH | O | -CH₂-CH₃ | -N=CH-CH=CH- | *(1:2)/ mp. 230.0° C. |
| 69 | CH₃-O-C₆H₄-CH₂-CH₂- | 2 | NH | O | -CH₂-CH₃ | -CH=CH-CH=CH- | *(1:2)/ mp. 177.1° C. |
| 70 | (tetrahydropyrido-pyrimidinone substituent)-CH₂-CH₂- | 1 | NH | O | -CH₂-CH₃ | -N=CH-CH=CH- | ½H₂O/ mp. 94.9° C. |
| 71 | (pyrido-pyrimidinone substituent)-CH₂-CH₂- | 2 | NH | O | -CH₂-CH₃ | -CH=CH-CH=CH- | 3(COOH)₂/ mp. 100.4° C. |
| 72 | (thiazole substituent)-CH₂-CH₂- | 1 | CH₂ | O | -CH₂-CH₃ | -N=CH-CH=CH- | 2.5(COOH) mp. 157.2° C. |

TABLE -continued

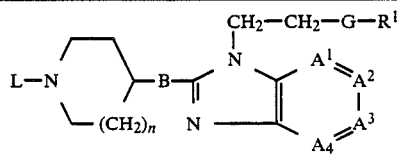

| Comp. No. | L | n | B | G | R¹ | A¹=A²—A³=A⁴ | Physical data |
|---|---|---|---|---|---|---|---|
| 73 | [structure: theophylline-like with CH₃, N-CH₃, H₃C-N, O, (CH₂)₂—] | 1 | CH₂ | O | —CH₂—CH₃ | —N=CH—CH=CH— | *(1:2)/ mp. 134.9° C. |
| 74 | [structure: S, N, CH₃, N, O, CH₂—CH₂—] | 1 | CH₂ | O | —CH₂—CH=CH₂ | —N=CH—CH=CH— | 2(COOH)₂/H₂O mp. 104.6° C. |

\* = (E)-2-butenedioate
There are also prepared following similar procedures:
1-[(2-methoxyethoxy)methyl]-N-[1-[2-(4-methoxyphenyl)ethyl]-4-piperidinyl]-1H-benzimidazol-2-amine (compound 75) and 1-[(2-methoxyethoxy)methyl]-N-[1-(2-ethoxyethyl)-4-piperidinyl]-1H-benzimidazol-2-amine (compound 76).

There are also prepared following similar procedures:
1-[(2-methoxyethoxy)methyl]-N-[1-[2-(4-methoxyphenyl)ethyl]-4-piperidinyl]-1H-benzimidazol-2-amine (compound 75) and
1-[(2-methoxyethoxy)methyl]-N-[1-(2-ethoxyethyl)-4-piperidinyl]-1H-benzimidazol-2-amine (compound 76).

Example 21

A mixture of 6 parts of 1-(2-bromoethyl)-1,3-dihydro-2H-benzimidazol-2-one, 7.63 parts of 2-[2-[2-(4-piperidinylamino)-3H-imidazo[4,5-b]pyridin-2-yl]ethoxy]ethanol, 3 parts of sodium carbonate and 47 parts of N,N-dimethylacetamide was stirred overnight at 70° C. After cooling, the reaction mixture was poured into water and the product was extracted with dichloromethane. The extract was dried, filtered and evaporated. The residue was purified by column chromatography over silica gel using a mixture of trichloromethane and methanol, saturated with ammonia (95:5 by volume) as eluent. The pure fractions were collected and the eluent was evaporated. The residue was crystallized twice from 2-propanone. The product was filtered off and dried, yielding 6.8 parts (58.4%) of 1,3-dihydro-1-[2-[4-[[3-[2-(2-hydroxyethoxy)ethyl]-3H-imidazo[4,5-b]pyridin-2-yl]amino]-1-piperidinyl]ethyl]-2H-benzimidazol-2-one; mp. 177.0° C. (compound 77).

In a similar manner there were also prepared:

TABLE

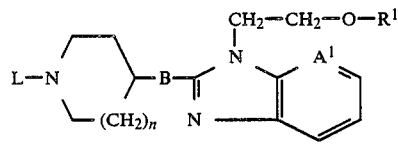

| Comp. No. | L | n | B | R¹ | A¹ | Physical data |
|---|---|---|---|---|---|---|
| 78 | [structure: benzimidazolone HN-C(=O)-N-CH₂-CH₂—] | 1 | O | —CH₂—CH₃ | CH | mp. 122.7° C. |
| 79 | [structure: benzimidazolone HN-C(=O)-N-CH₂-CH₂—] | 1 | NH | —CH₂—CH₂OH | CH | mp. 184.0° C. |

TABLE-continued
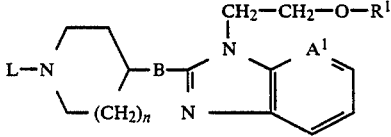
| Comp. No. | L | n | B | R¹ | A¹ | Physical data |
|---|---|---|---|---|---|---|
| 80 | 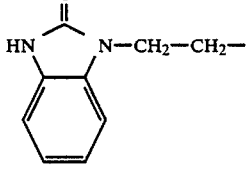 | 1 | $CH_2$ | $-CH_2-CH_3$ | N | 2 HCl/1.5 H$_2$O/ mp. 167.0° C. |
| 81 | 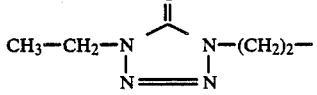 | 1 | NH | $-CH_2-CH_3$ | N | *(1:2)/ mp. 186.2° C. |
| 82 | 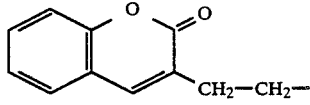 | 1 | NH | $-CH_2-CH_3$ | N | mp. 139.8° C. |
| 83 | 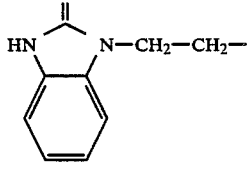 | 2 | NH | $-CH_2-CH_3$ | CH | *(1:2)/ mp. 134.3° C. |
| 84 | 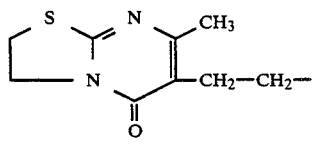 | 1 | NH | $-CH_2-CH_3$ | N | mp. 139.5° C. |
| 85 | 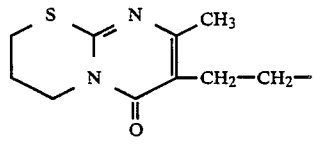 | 1 | NH | $-CH_2-CH_3$ | N | *(1:2)/ mp. 204.4° C. |
| 86 | 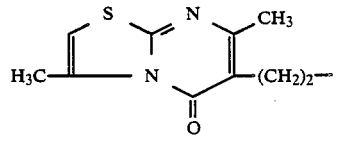 | 1 | NH | $-CH_2-CH_3$ | N | mp. 151.0° C. |
| 87 | 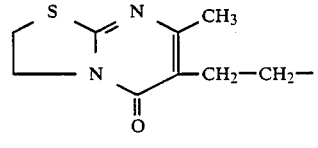 | 1 | $CH_2$ | $-CH_2-CH_3$ | N | *(2:1)/ mp. 203.0° C. |
| 88 | 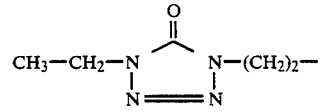 | 1 | $CH_2$ | $-CH_2-CH_3$ | N | 2 (COOH)$_2$/ mp. 142.2° C. |

TABLE-continued

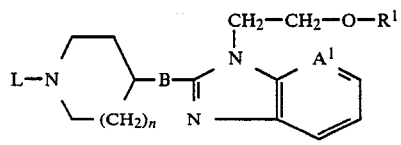

| Comp. No. | L | n | B | R¹ | A¹ | Physical data |
|---|---|---|---|---|---|---|
| 89 | ![benzimidazolone-N-CH₂-CH₂-] | 2 | NH | —CH₂—CH₃ | N | 2 (COOH)₂/ mp. 169.4° C. |
| 90 | ![coumarin-CH₂-CH₂-] | 1 | CH₂ | —CH₂—CH₃ | N | (3:2)/0.5 ethanol mp. 125.7° C. |

*(E)-2-butenedioate

Example 22

A mixture of 3.1 parts of 2-thiopheneethanol methanesulfonate(ester), 7 parts of 3-(2-ethoxyethyl)-N-(4-piperidinyl)-3H-imidazo[4,5-b]pyridin-2-amine ethanedioate(1:2), 1.6 parts of sodium carbonate and 75 parts of N,N-dimethylacetamide was stirred overnight at 80° C. The reaction mixture was poured into water and the product was extracted with 4-methyl-2-pentanone. The extract was dried, filtered and evaporated. The residue was purified by column chromatography over silica gel using a mixture of trichloromethane and methanol (96:4 by volume) as eluent. The pure fractions were collected and the eluent was evaporated. The residue was converted into the ethanedioate salt in methanol. The salt was filtered off and dried, yielding 4.59 parts (52.7%) of 3-(2-ethoxyethyl)-N-[1-[2-(2-thienyl)ethyl]-4-piperidinyl]-3H-imidazo[4,5-b]-pyridin-2-amine ethanedioate(1:2); mp. 218.2° C. (compound 91).

Example 23

A mixture of 9.4 parts of 2-chloroacetonitrile, 30 parts of 3-(2-ethoxyethyl)-N-(4-piperidinyl)-3H-imidazo[4,5-b]pyridin-2-amine, 11 parts of sodium carbonate and 658 parts of N,N-dimethylformamide was stirred over weekend at room temperature. The reaction mixture was poured into water and the product was extracted with dichloromethane. The extract was dried, filtered and evaporated. The residue was purified by column chromatography over silica gel using a mixture of trichloromethane and methanol (97:3 by volume) as eluent. The pure fractions were collected and the eluent was evaporated. The residue was stirred in 2,2'-oxybispropane. The product was filtered off and dried in vacuo, yielding 7.2 parts (21.0%) of 4-[[3-(2-ethoxyethyl)-3H-imidazo[4,5-b]pyridin-2-yl]amino]-1-piperidineacetonitrile; mp. 141.4° C. (compound 92).

In a similar manner there were also prepared:
N-[1-[(2,3-dihydro-1,4-benzodioxin-2-yl)methyl]-4-piperidinyl]-3-(2-ethoxyethyl)-3H-imidazo[4,5-b]pyridin-2-amine; mp. 140.7° C. (compound 93);

3-(2-ethoxyethyl)-N-[1-[(4-methyl-1H-imidazol-5-yl)methyl]-4-piperidinyl]-3H-imidazo[4,5-b]pyridin-2-amine; mp. 187.9° C. (compound 94);

ethyl 4-[[3-(2-ethoxyethyl)-3H-imidazo[4,5-b]pyridin-2-yl]amino]-1-piperidineacetate ethanedioate(1:2); mp. 186.5° C. (compound 95);

3-[2-[4-[[1-[2-(dimethylamino)ethyl]-1H-benzimidazol-2-yl]amino]-1-piperidinyl]ethyl]-2-methyl-4H-pyrido[1,2-a]pyrimidin-4-one (E)-2-butenedioate(2:5) 2-propanolate(1:1); mp. 174.6° C. (compound 96);

3-[2-[4-[[3-[2-(diethylamino)ethyl]-3H-imidazo[4,5-b]pyridin-2-yl]amino]-1-piperidinyl]ethyl]-2-methyl-4H-pyrido[1,2-a]pyrimidin-4-one (E)-2-butenedioate(1:2) monohydrate; mp. 132.3° C. (compound 97) and 6-[2-[4-[[3-(2-ethoxyethyl)-3H-imidazo[4,5-b]pyridin-2-yl]methyl]-1-piperidinyl]ethyl]-7-methyl-5H-thiazolo[3,2-a]pyrimidin-5-one (E)-2-butenedioate(2:3) hemihydrate; mp. 152.4° C. (compound 98).

Example 24

A mixture of 3.7 parts of [(2-bromoethyl)sulfonyl]-benzene, 4.34 parts of 3-(2-ethoxyethyl)-N-(4-piperidinyl)-3H-imidazo[4,5-b]pyridin-2-amine, 2.5 parts of sodium hydrogen carbonate and 120 parts of ethanol was stirred for 2 hours at reflux temperature. The reaction mixture was filtered over diatomaceous earth and the filtrate was evaporated. The residue was taken up in water and the product was extracted with 4-methyl-2-pentanone. The extract was dried, filtered and evaporated. The residue was purified by column chromatography over silica gel using a mixture of trichloromethane and methanol (97:3 by volume) as eluent. The pure fractions were collected and the eluent was evaporated. The residue was crystallized from a mixture of tetrahydrofuran and 2,2'-oxybispropane. The product was filtered off and dried, yielding 2.6 parts (37.1%) of 3-(2-ethoxyethyl)-N-[1-[2-(phenylsulfonyl)ethyl]-4-piperidinyl]-3H-imidazo-[4,5-b]pyridin-2-amine hemihydrate; mp. 101.9° C. (compound 99).

In a similar manner there were also prepared:

3-(2-ethoxyethyl)-N-[1-[2-(phenylthio)ethyl]-4-piperidinyl]-3H-imidazo [4,5-b]-pyridin-2-amine; mp. 102.5° C. (compound 100);

4-[[3-(2-ethoxyethyl)-3H-imidazo[4,5-b]pyridin-2-yl]amino]-N-(1-methylethyl)-1-piperidinepropanamide; mp. 163.7° C. (compound 101);

3-(2-ethoxyethyl)-N-[1-(2-propenyl)-4-piperidinyl]-3H-imidazo[4,5-b]pyridin-2-amine ethanedioate(1:2); mp. 183.8° C. (compound 102) and 4-[[3-(2-ethoxyethyl)-3H-imidazo[4,5-b]pyridin-2-yl]methyl]-N-(1-methylethyl)-1-piperidinepropanamide; mp. 97.8° C. (compound 103).

Example 25

A mixture of 4.53 parts of chloroacetonitrile, 17.3 parts of 3-(2-ethoxyethyl)-2-(4-piperidinylmethyl)-3H-imidazo[4,5-b]pyridine, 6 parts of N,N-diethylethanamine and 94 parts of N,N-dimethylformamide was stirred for 3 hours at room temperature. The reaction mixture was poured into water and the product was extracted with 1,1'-oxybisethane. The extract was dried, filtered and evaporated, yielding 23.75 parts (100%) of 4-[[3-(2-ethoxyethyl)-3H-imidazo[4,5-b]pyridin-2-yl]methyl]-1-piperidineacetonitrile as a residue (compound 104).

Example 26

To a stirred mixture of 2.6 parts of 2-(4-piperidinylamino)-3H-imidazo[4,5-b]pyridine-3-ethanol and 90 parts of N,N-dimethylformamide were added 0.5 parts of a sodium hydride dispersion 50%. After stirring for 30 minutes at room temperature, 1.2 parts of 3-bromo-1-propene were added dropwise while cooling. Upon complete addition, stirring was continued for 1 hour. The reaction mixture was poured into water and the product was extracted with trichloromethane. The extract was dried, filtered and evaporated. The residue was purified by column chromatography over silica gel using a mixture of trichloromethane and methanol, saturated with ammonia, (96:4 by volume) as eluent. The pure fractions were collected and the eluent was evaporated. The residue was converted into the ethanedioate salt in ethanol. The salt was filtered off and dried, yielding 1 part (20.7%) of 2-[[1-(2-propenyl)-4-piperidinyl]amino]-3H-imidazo[4,5-b]pyridine-3-ethanol ethanedioate(1:2); mp. 188.4° C. (compound 105).

Example 27

To a stirred and cooled (0° C.) mixture of 4.34 parts of 3-(2-ethoxyethyl)-N-(4-piperidinyl)-3H-imidazo[4,5-b]pyridin-2-amine, 1.53 parts of N,N-diethylethanamine and 130 parts of dichloromethane was added dropwise a solution of 1.63 parts of ethyl carbonochloridate in dichloromethane. Upon complete addition, the temperature was allowed to reach room temperature. The mixture was washed with water and the separated organic layer was dried, filtered and evaporated. The residue was purified by column chromatography over silica gel using a mixture of trichloromethane and ethanol (95:5 by volume) as eluent. The pure fractions were collected and the eluent was evaporated. The residue was converted into the (E)-2-butenedioate salt in ethanol. The salt was filtered off and dried, yielding 2.02 parts (25.1%) of ethyl 4-[[3-(2-ethoxyethyl)-3H-imidazo[4,5-b]pyridin-2-yl]amino]-1-piperidinecarboxylate (E)-2-butenedioate(2:3); mp. 153.8° C. (compound 106).

In a similar manner there was also prepared:
ethyl 4-[[1-(2-ethoxyethyl)-1H-imidazo[4,5-c]pyridin-2-yl]amino]-1-piperidinecarboxylate ethanedioate(2:5); mp. 157.5° C. (compound 107).

Example 28

A mixture of 3 parts of 3-(2-ethoxyethyl)-N-(4-piperidinyl)-3H-imidazo[4,5-b]pyridin-2-amine, 3 parts of poly(oxymethylene), 1 part of a solution of thiophene in methanol 4%, 120 parts of methanol and 5 parts of acetic acid, potassium salt was hydrogenated at normal pressure and at room temperature with 2 parts of palladium-on-charcoal catalyst 10%. After the calculated amount of hydrogen was taken up, the catalyst was filtered off over diatomaceous earth and the filtrate was evaporated. The residue was taken up in water and treated with a sodium hydroxide solution. The product was extracted with dichloromethane. The extract was dried, filtered and evaporated. The residue was converted into the hydrochloride salt in 2-propanone and 2-propanol. The salt was filtered off and dried, yielding 2 parts (72.8%) of 3-(2-ethoxyethyl)-N-(1-methyl-4-piperidinyl)-3H-imidazo[4,5-b]pyridin-2-amine dihydrochloride; mp. 260.4° C. (compound 108).

In a similar manner there were also prepared:

TABLE

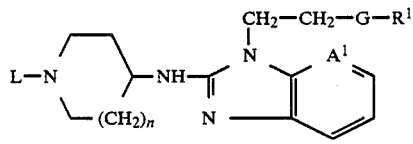

| Comp. No. | L | n | G | R¹ | A¹ | Physical data |
|---|---|---|---|---|---|---|
| 109 | $CH_3-$ | 1 | S | $-CH_2$ ⟨O⟩ | N | (E)-2-butenedioate(1:2)/ mp. 191.8° C. |
| 110 | $CH_3-$ | 1 | O | $-CH_2$ ⟨O⟩ | N | mp. 136.2° C. |
| 111 | $CH_3-$ | 1 | O | $-CH_2-CH_2OH$ | N | mp. 117.0° C. |
| 112 | $C_6H_{11}$-c | 1 | O | $-CH_2-CH_3$ | N | 2 $(COOH)_2$/mp. 202.2° C. |
| 113 | $CH_3-$ | 2 | O | $-CH_2-CH_3$ | CH | 2 $(COOH)_2$/mp. 179.7° C. |
| 114 | $(CH_3)_2-CH-$ | 1 | O | $-CH_2-CH_3$ | N | 2 $(COOH)_2$/mp. 200.0° C. |

TABLE-continued

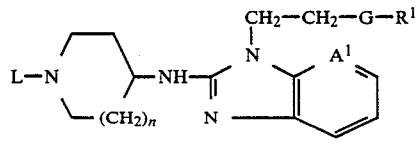

| Comp. No. | L | n | G | R¹ | A¹ | Physical data |
|---|---|---|---|---|---|---|
| 115 | CH₃—CH₂— | 1 | O | —CH₂—CH₃ | N | 2 (COOH)₂/mp. 200.5° C. |
| 116 | CH₃— | 0 | O | —CH₂—CH₃ | N | 2 (COOH)₂/mp. 159.2° C. |
| 117 | CH₃— | 2 | O | —CH₂—CH₃ | N | 2 (COOH)₂/mp. 159.3° C. |

In a similar manner there are also prepared:
1-[(2-methoxyethoxy)methyl]-N-(1-methyl-4-piperidinyl)-1H-benzimidazol-2-amine (compound 118) and
N-ethyl-N-[2-[2-[(1-methyl-4-piperidinyl)amino]-3H-imidazo[4,5-b]pyridin-1-yl]ethyl]acetamide (compound 119).

Example 29

A mixture of 28 parts of 2-(4-piperidinylamino)-3H-imidazo[4,5-b]pyridine-3-ethanol, 20 parts of benzaldehyde, 2 parts of a solution of thiophene in methanol 4% and 160 parts of methanol was hydrogenated at normal pressure and at room temperature with 3 parts of palladium-on-charcoal catalyst 10%. After the calculated amount of hydrogen was taken up, the catalyst was filtered off and the filtrate was evaporated. The residue was taken up in trichloromethane and the whole was extracted with an acidic aqueous solution. The extract was washed three times with trichloromethane and treated with a sodium hydroxide solution. The product was extracted with dichloromethane. The extract was dried, filtered and evaporated. The residue was stirred in 1,1'-oxybisethane. The solid product was filtered off and dried, yielding 25.2 parts (65.1%) of 2-[[1-(phenylmethyl)-4-piperidinyl]amino]-3H-imidazo[4,5-b]pyridine-3-ethanol; mp. 125.7° C. (compound 120).

In a similar manner there were also prepared:

din-2-amine, 1.6 parts of sodium carbonate and 47 parts of N,N-dimethylacetamide was stirred overnight at 120° C. After cooling, the reaction mixture was poured into water and the product was extracted with trichloromethane. The extract was dried, filtered and evaporated. The residue was purified by column chromatography over silica gel using a mixture of trichloromethane and methanol, saturated with ammonia, (97:3 by volume) as eluent. The pure fractions were collected and the eluent was evaporated. The residue was converted into the ethanedioate salt in ethanol. The salt was filtered off and dried, yielding 1.23 parts (13.2%) of 3-(2-ethoxyethyl)-N-[1-[2-[(5-methyl-1,3,4-thiadiazol-2-yl)amino]ethyl]-4-piperidinyl]-3H-imidazo[4,5-b]pyridin-2-amine ethanedioate(1:2), hemihydrate; mp. 197.3° C. (compound 129). In a similar manner there is also prepared:
N-[2-[4-[[3-(2-ethoxyethyl)-3H-imidazo[4,5-b]pyridin-2-yl]methyl]-1-piperidinyl]ethyl]thiazol-2-amine (compound 130).

Example 31

A mixture of 1.7 parts of 2-chloropyrimidine, 4.33 parts of 4-[[3-(2-ethoxyethyl)-3H-imidazo[4,5-b]pyridin-2-yl]methyl]-1-piperidineethanamine, 1.7 parts of sodium hydrogen carbonate and 40 parts of ethanol was stirred overnight at reflux temperature. The reaction mixture was evaporated and the residue was poured

TABLE

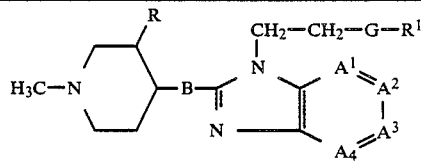

| Comp. No. | R | B | G | R¹ | A¹=A²—A³=A⁴ | Physical data |
|---|---|---|---|---|---|---|
| 121 | —H | NH | O | —H | —N=CH—CH=CH— | 2 HCl/2 H₂O/mp. 247.3° C. |
| 122 | —H | NH | O | —CH₂—CH₂OH | —CH=CH—CH=CH— | 2 (COOH)₂/mp. 181.3° C. |
| 123 | —H | NH | O | —CH₂—CH₃ | —CH=CH—N=CH— | mp. 142.3° C. |
| 124 | —H | NH | O | —CH₂—CH₃ | —N=CH—N=CH— | mp. 99.6° C. |
| 125 | —H | NH | O | —CH₂—CH₃ | —CH=N—CH=CH— | (E)-2-butenedioate(1:3) mp. 167.4° C. |
| 126 | —H | CH₂ | O | —CH₂—CH₃ | —N=CH—CH=CH— | (E)-2-butenedioate(1:2) mp. 143.2° C. |
| 127 | —H | NH | N | —(CH₂—CH₃)₂ | —N=CH—CH=CH— | (E)-2-butenedioate(2:7) mp. 193.3° C. |
| 128 | —CH₃ | NH | O | —CH₂—CH₃ | —N=CH—CH=CH— | 1½ (COOH)₂/0.5 H₂O cis/mp. 140.5° C. |

Example 30

A mixture of 2.4 parts of 2-bromo-5-methyl-1,3,4-thiadiazole, 5 parts of N-[1-(2-aminoethyl)-4-piperidinyl]-3-(2-ethoxyethyl)-3H-imidazo[4,5-b]pyriinto water. The product was extracted with trichloromethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the ethanedioate salt in a mixture of ethanol and 2-propanone. The salt was filtered off and dried, yielding 4.97 parts (48.7%) of N-[2-[4-[[3-(2-ethoxyethyl)-3H-imidazo[4,5-b]pyridin-2-yl]methyl]-1-piperidinyl]ethyl]-2-pyrimidinamine ethanedioate(1:3); mp. 119.7° C. (compound 131).

In a similar manner there was also prepared:
3-(2-ethoxyethyl)-N-[1-[2-(2-pyrimidinylamino)ethyl]-4-piperidinyl]-3H-imidazo[4,5-b]pyridin-2-amine; mp. 149.6° C. (compound 132).

Example 32

To a stirred mixture of 1 part of a sodium hydride dispersion 50% and 94 parts of N,N-dimethylformamide was added dropwise a solution of 5.5 parts of 4-[[3-(2-ethoxyethyl)-3H-imidazo[4,5-b]pyridin-2-yl]amino]-1-piperidineethanol in N,N-dimethylformamide. Upon complete addition, stirring was continued for 15 minutes at room temperature. 1.9 Parts of 2-chloropyrimidine were added portionwise and upon completion, stirring was continued for 2 hours at room temperature. The reaction mixture was decomposed with water and the product was extracted with dichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was converted into the ethanedioate salt in ethanol. The salt was filtered off and dried, yielding 3.4 parts (34.8%) of 3-(2-ethoxyethyl)-N-[1-[2-(2-pyrimidinyloxy)ethyl]-4-piperidinyl]-3H-imidazo-[4,5-b]pyridin-2-amine ethanedioate(1:2); mp. 185.7° C. (compound 133).

In a similar manner there was also prepared:
3-(2-ethoxyethyl)-2-[[1-[2-(2-pyrimidinyloxy)ethyl]4-piperidinyl]methyl]-3H-imidazo-[4,5-b]pyridine ethanedioate(1:2); mp. 140.2° C. (compound 134).

Example 33

A mixture of 1.5 parts of isothiocyanatomethane, 6.6 parts of N-[1(2-aminoethyl)-4-piperidinyl]-3-(2-ethoxyethyl)-3H-imidazo[4,5-b]pyridin-2-amine and 135 parts of tetrahydrofuran was stirred overnight at room temperature. The reaction mixture was evaporated and the residue was purified by column chromatography over silica gel using a mixture of trichloromethane and methanol (96:4 by volume) as eluent. The pure fractions were collected and the eluent was evaporated. The residue was converted into the ethanedioate salt in ethanol. The salt was filtered off and dried, yielding 1.2 parts (9.9%) of N-[2-[4-[[3-(2-ethoxyethyl)-3H-imidazo[4,5-b]pyridin-2-yl]amino]-1-piperidinyl]ethyl]-N'-mthylthiourea ethanedioate(1:2), monohydrate; mp. 166.8° C. (compound 135).

Example 34

To a stirred and cooled (−10° C.) mixture of 15 parts of carbon disulfide, 6.2 parts of N,N-methanetetraylbis[cyclohexanamine] and 90 parts of tetrahydrofuran was added dropwise a solution of 8.6 parts of 4-[[3-(2-ethoxyethyl)-3H-imidazo[4,5-b]pyridin-2-yl]methyl]-1-piperidineethanamine in tetrahydrofuran. Upon complete addition, the reaction mixture was stirred for 1 hour at room temperature. The whole was evaporated, yielding 11.2 parts (100%) of 3-(2-ethoxyethyl)-2-[[1-(2-isothiocyanatoethyl)-4-piperidinyl]methyl]-3H-imidazo[4,5-b]pyridine as a residue (compound 136).

In a similar manner there was also prepared:
3-(2-ethoxyethyl)-N-[1-(2-isothiocyanatoethyl)-4-piperidinyl]-3H-imidazo[4,5-b]pyridin-2-amine as a residue (compound 137).

Example 35

A mixture of 3.3 parts of 3,4-pyridinediamine, 11.2 parts of 3-(2-ethoxyethyl)-2-[[1-(2-isothiocyanatoethyl)-4-piperidinyl]methyl]-3H-imidazo[4,5-b]-pyridine and 90 parts of tetrahydrofuran was stirred overnight at reflux temperature. The reaction mixture was evaporated, yielding 14.5 parts (100%) of N-(4-amino-3-pyridinyl)-N'-[2-[4-[[3-(2-ethoxyethyl)-3H-imidazo[4,5-b]pyridin-2-yl]methyl]-1-piperidinyl]ethyl]thiourea as a residue (compound 138).

In a similar manner there was also prepared:
N-(4-amino-3-pyridinyl)-N'-[2-[4-[[3-(2-ethoxyethyl)-3H-imidazo[4,5-b]pyridin-2-yl]amino]-1-piperidinyl]ethyl]thiourea as a residue (compound 139).

Example 36

A mixture of 14.5 parts of N-(4-amino-3-pyridinyl)-N'-[2-[4-[[3-(2-ethoxyethyl)-3H-imidazo[4,5-b]pyridin-2-yl]methyl]-1-piperidinyl]ethyl]thiourea, 9.7 parts of mercury(II) oxide and 90 parts of tetrahydrofuran was stirred for 1 hour at reflux temperature. The reaction mixture was filtered while hot over diatomaceous earth and the filtrate was evaporated. The residue was purified by column chromatography over silica gel using a mixture of trichloromethane and methanol, saturated with ammonia, (90:10 by volume) as eluent. The pure fractions were collected and the eluent was evaporated. The residue was converted into the (E)-2-butenedioate salt in ethanol. The salt was filtered off and dried in a dry pistol at 90° C., yielding 6.78 parts (24.5%) of N-[2-[4-[[3-(2-ethoxyethyl)-3H-imidazo[4,5-b]pyridin-2-yl]methyl]-1-piperidinyl]ethyl]-1H-imidazo[4,5-c]pyridin-2-amine (E)-2-butenedioate(1:4), hemihydrate; mp. 171.4° C. (compound 140).

In a similar manner there was also prepared:
3-(2-ethoxyethyl)-N-[1-[2-[(1H-imidazo[4,5-c]pyridin-2-yl)amino]ethyl]-4-piperidinyl]-3H-imidazo[4,5-b]pyridin-2-amine (E)-2-butenedioate(2:9); mp. 193.6° C. (compound 141).

Example 37

To a stirred mixture of 1.12 parts of 3-furancarboxylic acid, 2.02 parts of N,N-diethylethanamine and 195 parts of dichloromethane were added 2.6 parts of 2-chloro-1-methylpyridinium iodide at room temperature. After stirring for 1 hour, 3.3 parts of N-[1-(2-aminoethyl)-4-piperidinyl]-3-(2-ethoxyethyl)-3H-imidazo[4,5-b]pyridin-2-amine were added and stirred overnight at room temperature. The mixture was poured into water and the layers were separated. The organic layer was dried, filtered and evaporated. The residue was purified by column chromatography over silica gel using a mixture of trichloromethane and methanol (96:4 by volume) as eluent. The pure fractions were collected and the eluent was evaporated. The residue was converted into the ethanedioate salt in ethanol. The salt was filtered off and dried, yielding 2.19 parts (36.1%) of N-[2-[4-[[3-(2-ethoxyethyl)-3H-imidazo[4,5-b]pyridin-2-yl]amino]-1- piperidinyl]ethyl]-3-furancarboxamide ethanedioate(1:2); mp. 160.7° C. (compound 142).

In a similar manner there were also prepared:
N-[2-[4-[[3-(2-ethoxyethyl)-3H-imidazo[4,5-b]pyridin-2-yl]amino]-1-piperidinyl]ethyl]-1-methyl-1H-pyrrole-2-carboxamide ethanedioate(1:2); mp. 188.0° C. (compound 143);
N-[2-[4-[[3-(2-ethoxyetyyl)-3H-imidazo[4,5-b]pyridin-2-yl]methyl]-1-piperidinyl]ethyl]-2-thiazolecarboxamide; mp. 116.7° C. (compound 144);
N-[2-[4-[[3-(2-ethoxyethyl)-3H-imidazo[4,5-b]pyridin-2-yl]methyl]-1-piperidinyl]ethyl]-3-furancarboxamide ethanedioate(1:1); mp. 207.5° C. (compound 145) and
N-[2-[4-[[3-(2-ethoxyethyl)-3H-imidazo[4,5-b]pyridin-2-yl]methyl]-1-piperidinyl]ethyl-1-methyl-1H-pyrrole-2-carboxamide; mp. 145.2° C. (compound 146).

In a similar manner there is also prepared:
2-amino-N-[2-[4-[[3-(2-ethoxyethyl)-3H-imidazo[4,5-b]pyridin-2-yl]methyl]-1-piperidinyl]ethyl]benzamide (compound 147).

Example 38

Through a stirred mixture of 8.7 parts of 3-(2-ethoxyethyl)-N-(4-piperidinyl)-3H-imidazo[4,5-b]pyridin-2-amine and 160 parts of methanol was bubbled oxirane during 15 minutes. After stirring for 2 hours at room temperature, the mixture was evaporated. The residue was purified by column chromatography over silica gel using a mixture of trichloromethane and methanol, saturated with ammonia, (95:5 by volume) as eluent. The pure fractions were collected and the eluent was evaporated. The residue was stirred in 2,2'-oxybispropane. The product was filtered off and dried, yielding 4.4 parts (43.9%) of 4-[[3-(2-ethoxyethyl)-3H-imidazo[4,5-b]pyridin-2-yl]amino]-1-piperidineethanol; mp. 94.3° C. (compound 148).

In a similar manner there was also prepared:
4-[[3-(2-ethoxyethyl)-3H-imidazo[4,5-b]pyridin-2-yl]methyl]-1-piperidineethanol (E)-2-butenedioate(2:3); mp. 146.8° C. (compound 149).

Example 39

A mixture of 5.4 parts of 2-(phenoxymethyl)oxirane, 7.0 parts of 3-(2-ethoxyethyl)-N-(4-piperidinyl)-3H-imidazo[4,5-b]pyridin-2-amine ethanedioate(1:2), 6.4 parts of sodium carbonate and 64 parts of 2-propanol was stirred for 20 hours at reflux temperature. The reaction mixture was evaporated and the residue was taken up in water. The product was extracted with 4-methyl-2-pentanone. The extract was dried, filtered and evaporated. The residue was purified by column chromatography over silica gel using a mixture of trichloromethane and methanol (95:5 by volume) as eluent. The pure fractions were collected and the eluent was evaporated. The residue was converted into the hydrochloride salt in a mixture of 2-propanol and ethanol. The salt was filtered off and dried, yielding 3.1 parts (40.3%) of 4-[[3-(2-ethoxyethyl)-3H-imidazo[4,5-b]pyridin-2-yl]amino]-α-(phenoxymethyl)-1-piperidineethanol dihydrochloride; mp. 250.7° C. (compound 150).

Example 40

A mixture of 1.58 parts of 2-ethenylpyridine, 7 parts of 3-(2-ethoxyethyl)-N-(4-piperidinyl)-3H-imidazo[4,5-b]pyridin-2-amine ethanedioate (1:2), 1.8 parts of sodium carbonate and 80 parts of 1-butanol was stirred overnight at reflux temperature. The reaction mixture was evaporated and the residue was taken up in trichloromethane. The organic layer was washed twice with water, dried, filtered and evaporated. The residue was converted into the hydrochloride salt in 2-propanol. The salt was filtered off and dried in a dry pistol at 100° C., yielding 1.67 parts (21.7%) of 3-(2-ethoxyethyl)-N-[1-[2-(2-pyridinyl)ethyl]-4-piperidinyl]-3H-imidazo-[4,5-b]pyridin-2-amine trihydrochloride, hemihydrate; mp. 229.1° C. (compound 151).

In a similar manner there was also prepared:
3-(2-ethoxyethyl)-2-[[1-[2-(2-pyridinyl)ethyl]-4-piperidinyl]methyl]-3H-imidazo-[4,5-b]pyridine ethanedioate(1:3); mp. 157.8° C. (compound 152).

Example 41

To a stirred mixture of 4.32 parts of N-[1-(2-ethoxyethyl)-4-piperidinyl]-1H-benzimidazol-2-amine and 135 parts of N,N-dimethylformamide were added 0.75 parts of a sodium hydride dispersion 50% under nitrogen atmosphere. After stirring for 30 minutes at room temperature, a solution of 1.63 parts of 1-chloro-2-ethoxyethane in N,N-dimethylformamide was added dropwise to the thus obtained mixture at 50° C. Upon complete addition, stirring was continued overnight at 50° C. The reaction mixture was poured into water and the product was extracted with 4-methyl-2-pentanone. The extract was dried, filtered and evaporated. The residue was purified by column chromatography over silica gel using a mixture of trichloromethane and methanol, saturated with ammonia, (98:2 by volume) as eluent. The pure fractions were collected and the eluent was evaporated. The residue was converted into the ethanedioate salt in ethanol. The salt was filtered off and dried, yielding 3.2 parts (39.5%) of 1-(2-ethoxyethyl)-N-[1-(2-ethoxyethyl)-4-piperidinyl]-1H-benzimidazol-2-amine ethanedioate(1:2); mp. 184.7° C. (compound 153).

In a similar manner there were also prepared:

TABLE

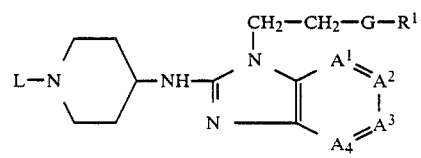

| Comp. No. | L | G | R¹ | A¹—A²—A³—A⁴ | Physical data |
|---|---|---|---|---|---|
| 154 | $CH_3-$ | O | $-CH_2-CH_3$ | $-CH=CH-CH=CH-$ | 2 $(COOH)_2$/ mp. 214.8° C. |

TABLE-continued $$\text{L-N} \underset{}{\overset{}{\bigcirc}} \text{-NH} - \underset{N}{\overset{\underset{|}{CH_2-CH_2-G-R^1}}{C}} \underset{}{\overset{A^1 \underset{A^4}{\overset{A^2}{\underset{|}{\parallel}}} A^3}{}}$$

| Comp. No. | L | G | R¹ | A¹—A²—A³—A⁴ | Physical data |
|---|---|---|---|---|---|
| 155 | CH₃—O—⟨phenyl⟩—(CH₂)₂— | O | —CH₂—CH₃ | —CH=CH—CH=CH— | 2 (COOH)₂/ mp. 230.0° C. |
| 156 | CH₃—CH₂—O—(CH₂)₂— | O | -phenyl | —CH=CH—CH=CH— | mp. 158.8° C. |
| 157 | CH₃— | O | -phenyl | —CH=CH—CH=CH— | mp. 154.1° C. |
| 158 | CH₃—O—⟨phenyl⟩—(CH₂)₂— | O | -phenyl | —CH=CH—CH=CH— | mp. 131.5° C. |
| 159 | CH₃— | O | —CH=CH₂ | —CH=CH—CH=CH— | mp. 128.8° C. |
| 160 | CH₃— | S | —CH₂—CH₃ | —CH=CH—CH=CH— | *(1:2) mp. 237.2° C. |
| 161 | CH₃— | O | —CH₃ | —CH=CH—CH=CH— | *(1:2) mp. 201.6° C. |
| 162 | CH₃— | O | —CH₂—CH₃ | —CH=C(OCH₃)—CH=CH— | mp. 121.2° C. |
| 163 | CH₃— | O | —CH₂—CH₃ | —CH=CH—C(OCH₃)=CH— | *(1:2) mp. 215.7° C. |
| 164 | CH₃— | O | —CH₂—CH₃ | —CH=CH—C(F)=CH— | *(1:2) mp. 213.2° C. |
| 165 | CH₃— | O | —CH₂—CH₃ | —CH=C(F)—CH=CH— | 2 (COOH)₂/ mp. 185.9° C. |
| 166 | CH₃— | O | —CH₂—CH₃ | —CH=C(OCH₃)—C(OCH₃)=CH— | *(1:2) mp. 194.4° C. |

*(E)-2-butenedioate and ethyl 4-[[1-[(methoxyethyoxy)methyl]-1H-benzimidazol-2-yl]amino]-1-piperidinecarboxylate; mp. 102.2° C. (compound 167).

Example 42

To a stirred mixture of 4.13 parts of 2-[(1-methyl-4-piperidinyl)amino]-3H-imidazo[4,5-b]pyridine-3-ethanol and 90 parts of N,N-dimethylformamide were added 0.75 parts of a sodium hydride dispersion 50%. After stirring for 30 minutes at room temperature, 1.7 parts of 2-chloropyrimidine were added. The whole was stirred for 1 hour at room temperature and the reaction mixture was poured into water. The product was extracted with trichloromethane. The extract was dried, filtered and evaporated. The residue was crystallized from acetonitrile. The product was filtered off and dried, yielding 1.7 parts (32.0%) of N-(1-methyl-4-piperdinyl)-3-[2-(2-pyrimidinyloxy)ethyl]-3H-imidazo[4,5-b]-pyridin-2-amine; mp. 158.1° C. (compound 168).

In a similar manner there were also prepared:

N-(4-piperidinyl)-3-[2-(2-pyrimidinyloxy)ethyl]-3H-imidazo[4,5-b]pyridin-2-amine ethanedioate(1:2); mp. 172.4° C. (compound 169);

N-(1-methyl-4-piperidinyl)-3-[2-(2-propenyloxy)ethyl]-3H-imidazo[4,5-b]pyridin-2-amine ethanedioate(1:2); mp. 188.1° C. (compound 170);

2-[[1-(phenylmethyl)-4-piperidinyl]methyl]-3-[2-(2-propenyloxy)ethyl]-3H-imidazo[4,5-b]pyridine as a residue (compound 171);

ethyl hexahydro-4-[[1-[2-(2-pyrimidinyloxy)ethyl]-1H-benzimidazol-2-yl]amino]-1H-azepine-1-carboxylate as a residue (compound 172) and N-(1-methyl-4-piperidinyl)-3-[2-(2-propynyloxy)ethyl]-3H-imidazo[4,5-b]pyridin-2-amine (E)-2-butenedioate(1:3); mp. 196.2° C. (compound 173).

Example 43

To a stirred solution of 11.9 parts of 2-[[1-(phenylmethyl)-4-piperidinyl]amino]-3H-imidazo[4,5-b]pyridine-3-ethanamine in 160 parts of N,N-dimethylformamide were added 4.41 parts of ethyl carbonochloridate and 4.05 parts of N,N-diethylethanamine. The reaction mixture was heated slowly to 50° C. and stirred first for 18 hours at this temperature and then for 18 hours at 70° C. The reaction mixture was evaporated and the residue was taken up in a solution of sodium carbonate in water. The product was extracted with dichloromethane. The extract was washed with water, dried, filtered and evaporated. The residue was purified by column chromatography over silica gel using a mixture of trichloromethane and methanol (90:10 by volume) as eluent. The pure fractions were collected and the eluent was evaporated. The residue was converted into the ethanedioate salt in 2-propanol. The salt was filtered off crystallized twice from ethanol. The product was filtered off and dried, yielding 6.6 parts (26.7%) of ethyl N-[2-[2-[[1-(phenylmethyl)-4-piperidinyl]amino]-3H-imidazo[4,5-b]-pyridin-3-yl]ethyl]glycine ethanedioate(1:3), monohydrate; mp. 169.5° C. (compound 174).

Example 44

A mixture of 1.6 parts of poly(oxymethylene), 8.1 parts of ethyl 4-[[1-(2-aminoethyl)-1H-benzimidazol-2-yl]amino]-1-piperidinecarboxylate and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was purified by column chromatography over silica gel using a mixture of trichloromethane and methanol, saturated with ammonia, (95:5 by volume) as eluent. The pure fractions were collected and the eluent was evaporated, yielding 9.2 parts (100%) of ethyl 4-[[1-[2-(dimethylamino)ethyl]-1H-benzimidazol-2-yl]amino]-1-piperidinecarboxylate as a residue (compound 175).

Example 45

7.8 Parts of N-ethyl-2-[[1-(phenylmethyl)-4-piperidinyl]amino]-3H-imidazo[4,5-b]pyridin-3-ethanamine were taken up in 75 parts of trichloromethane. 1.51 Parts of acetic acid anhydride were added (exothermic reaction). The reaction mixture was stirred for 18 hours at room temperature. The whole was filtered over silica gel using a mixture of trichloromethane and methanol, saturated with ammonia (95:5 by volume) as eluent. The pure fractions were collected and the eluent was evaporated. The residue was taken up in methylbenzene and the whole was evaporated again, yielding 8.5 parts (100%) of N-ethyl-N-[2-[2-[[1-(phenylmethyl)-4-piperidinyl]amino]-3H-imidazo[4,5-b]pyridin-3-yl]ethyl]acetamide as a residue (compound 176).

Example 46

A mixture of 2.7 parts of a sodium hydride dispersion 50% and 282 parts of N,N-dimethylformamide was stirred at room temperature under nitrogen atmosphere. 18.8 Parts of ethyl 4-[[3-(2-ethoxyethyl)-3H-imidazo[4,5-b]pyridin-2-yl]amino]-1-piperidinecarboxylate were added portionwise to the previous mixture. Upon complete addition, stirring for continued for 1 hour at room temperature. 10 Parts of (bromomethyl)benzene were added dropwise and upon completion, stirring was continued for 1 hour. The reaction mixture was decomposed with water and the product was extracted with 4-methyl-2-pentanone. The extract was dried, filtered and evaporated. The residue was purified by column chromatography over silica gel using a mixture of trichloromethane and ethanol (98:2 by volume) as eluent. The pure fractions were collected and the eluent was evaporated. The residue was crystallized from 2,2'-oxybispropane. The product was filtered off and dried, yielding 3.2 parts (13.6%) of ethyl 4-[[3-(2-ethoxyethyl)-3H-imidazo[4,5-b]pyridin-2-yl](phenylmethyl)amino]-1-piperidinecarboxylate; mp. 115.0° C. (compound 177).

In a similar manner there was also prepared:
ethyl 4-[[3-(2-ethoxyethyl)-3H-imidazo[4,5-b]pyridin-2-yl]methylamino]-1-piperidinecarboxylate as a residue (compound 178).

Example 47

A mixture of 23.75 parts of 4-[[3-(2-ethoxyethyl)-3H-imidazo[4,5-b]pyridin-2-yl]methyl]-1-piperidineacetonitrile and 400 parts of methanol, saturated with ammonia was hydrogenated at normal pressure and at room temperature with 6 parts of Raney nickel catalyst. After the calculated amount of hydrogen was taken up, the catalyst was filtered off and the filtrate was evaporated, yielding 22.7 parts (100%) of 4-[[3-(2-ethoxyethyl)-3H-imidazo[4,5-b]pyridin-2-yl]methyl]-1-piperidineethanamine as a residue (compound 179).

In a similar manner there was also prepared:
N-[1-(2-aminoethyl)-4-piperidinyl]-3-(2-ethoxyethyl)-3H-imidazo[4,5-b]pyridin-2-amine as a residue (compound 180).

Example 48

A mixture of 10.4 parts of ethyl 4-[[1-(cyanomethyl)-1H-benzimidazol-2-yl]amino]-1-piperidinecarboxylate and 160 parts of methanol, saturated with ammonia was hydrogenated at normal pressure and at room temperature with 2 parts of Raney nickel catalyst. After the calculated amount of hydrogen was taken up, the catalyst was filtered off and the filtrate was evaporated. The residue was purified by column chromatography over silica gel using a mixture of trichloromethane and methanol (90:10 by volume) as eluent. The pure fractions were collected and the eluent was evaporated. The residue was converted into the ethanedioate salt in 2-propanol. The salt was filtered off and crystallized from ethanol. The product was filtered off and dried, yielding 6.5 parts (39.5%) of ethyl 4-[[1-(2-aminoethyl)-1H-benzimidazol-2-yl]amino]-1-piperidinecarboxylate ethanedioate(1:2), monohydrate; mp. 176.1° C. (compound 181).

Example 49

A mixture of 5.5 parts of ethyl 4-[[3-(2-ethoxyethyl)-3H-imidazo[4,5-b]pyridin-2-yl]amino]-1-piperidineacetate, 15 parts of a sodium hydroxide solution 1N, 100 parts of water and 16 parts of ethanol was stirred overnight at room temperature. The reaction mixture was evaporated. The residue was taken up in water, washed with dichloromethane and purified by column chromatography over silica gel using a mixture of trichloromethane and methanol, saturated with ammonia, (80:20 by volume) as eluent. The pure fractions were collected and the eluent was evaporated. The residue was crystallized from 2-propanol. The product was filtered off and dried, yielding 1 part (19.1%) of 4-[[3-(2-ethoxyethyl)-3H-imidazo[4,5-b]pyridin-2-yl]amino]-1-piperidineacetic acid; mp. 227.3° C. (compound 182).

Example 50

2.4 Parts of a sodium hydride dispersion 50% were added portionwise to 147 parts of N,N-dimethylformamide under nitrogen atmosphere. Upon complete addition, 12.5 parts of N-[1-(2-ethoxyethyl)-4-piperidinyl]-

1H-benzimidazol-2-amine were added portionwise to the previous mixture. Upon completion, stirring was continued for 1 hour at room temperature. The whole was cooled and 9.85 parts of 2-(bromoethoxy)ethyl acetate were added (exothermic reaction). The reaction mixture was stirred for 2 hours at room temperature. The mixture was decomposed with water and the product was extracted with trichloromethane. The extract was dried, filtered and evaporated. A mixture of the residue and 160 parts of methanol, saturated with ammonia was stirrred for 5 hours at room temperature. The reaction mixture was evaporated and the residue was purified by column chromatography over silica gel, using a mixture of trichloromethane and methanol, saturated with ammonia (95:5 by volume) as eluent. The pure fractions were collected and the eluent was evaporated. The residue was crystallized from 4-methyl-2-pentanone. The product was filtered off and dried, yielding 0.98 parts (6.3%) of 2-[2-[2-[[1-(ethoxyethyl)-4-piperidinyl]amino]-1H-benzimidazol-1-yl]methoxy]ethanol; mp. 109.0° C. (compound 183).

In a similar manner there were also prepared:
ethyl 4-[[1-[(2-hydroxyethoxy)methyl]-1H-benzimidazol-2-yl]amino]-1-piperidinecarboxylate; mp. 142.8° C. (compound 184) and
2-[[2-[[1-[2-(4-methoxyphenyl)ethyl]-4-piperidinyl]amino]-1H-benzimidazol-1-yl]methoxy]ethanol; mp. 142.0° C. (compound 185).

In a similar manner there is also prepared:
2-[[2-[(1-methyl-4-piperidinyl)amino]-1H-benzimidazol-1-yl]methoxy]ethanol (compound 186).

Example 51

A mixture of 20 parts of ethyl [2-[2-[[1-(phenylmethyl)-4-piperidinyl]amino]-3H-imidazo[4,5-b]-pyridin-3-yl]ethyl]carbamate, 26.3 parts of potassium hydroxide and 200 parts of 2-propanol was stirred for 1.5 hour at reflux temperature. The reaction mixture was evaporated and the residue was taken up in water. The whole was evaporated again. The residue was taken up in a small amount of water and the product was extracted with dichloromethane. The extract was dried, filtered and evaporated. The residue was purified by column chromatography over silica gel using a mixture of trichloromethane and methanol, saturated with ammonia, (90:10 by volume) as eluent. The pure fractions were collected and the eluent was evaporated. The residue was boiled in 2,2'-oxybispropane (+activated charcoal) and the whole was filtered over diatomaceous earth. The filtrate was allowed to crystallize. The crystallized product was filtered off (the filtrate was set aside) and dried, yielding a first fraction of 6.7 parts (40.6%) of 2-[[1-(phenylmethyl)-4-piperidinyl]amino]-3H-imidazo[4,5-b]pyridine-3-ethanamine. The filtrate, which was set aside (see above) was evaporated, yielding a second fraction of 6.6 parts (40.0%) of 2-[[1-(phenylmethyl)-4-piperidinyl]amino]-3H-imidazo[4,5-b]pyridine-3-ethanamine. Total yield: 13.3 parts (80.6%) of 2-[[1-(phenylmethyl)-4-piperidinyl]amino]-3H-imidazo[4,5-b]pyridine-3-ethanamine; mp. 101.7° C. (compound 187).

In a similar manner there was also prepared:
N-ethyl-2-[[1-(phenylmethyl)-4-piperidinyl]amino]-3H-imidazo[4,5-b]pyridine-3-ethanamine trihydrochloride; mp. 279.4° C. (compound 188).

Example 52

To a stirred solution of 3.46 parts of ethyl N-[2-[2-(4-piperidinylamino)-3H-imidazo[4,5-b]pyridin-3-yl]ethyl]glycine and 25 parts of water were added 1.12 parts of potassium hydroxide. After stirring for 18 hours at room temperature, the reaction mixture was washed with dichloromethane and acidified with concentrated hydrochloric acid. The whole was evaporated to dry and the residue was purified by reversed phase chromatography (HPLC) over Li Chroprep RP 18 using a mixture of 80% of methanol and 20% of water containing 0.25% of ammonium acetate as eluent. The desired fraction was collected and the eluent was evaporated. The residue was converted into the hydrochloride salt in 2-propanol, ethanol and hexane. The salt was dried, yielding 1.18 parts (26.4%) of N-[2-[2-(4-piperidinylamino)-3H-imidazo[4,5-b]pyridin-3-yl]ethyl]glycine dihydrochloride, trihydrate; mp. 242.6° C. (compound 189).

In a similar manner there are also prepared:
α-[2-[2-[(1-methyl-4-piperidinyl)amino]-3H-imidazo[4,5-b]pyridin-3-yl]-ethyl]oxy]acetic acid (compound 190) and
α-[2-[2-[[1-(phenylmethyl)-4-piperidinyl]amino]-3H-imidazo[4,5-b]pyridin-3-yl]ethyl]oxy]acetic acid (compound 191).

Example 53

To a stirred mixture of 21 parts of a lithium tetrahydroaluminate solution 1M in 1,1'-oxybisethane in 45 parts of tetrahydrofuran was added dropwise a solution of 4.9 parts of ethyl 4-[[3-(2-ethoxymethyl)-3H-imidazo[4,5-b]pyridin-2-yl]methylamino]-1-piperidinecarboxylate in 45 parts of tetrahydrofuran during 10 minutes under nitrogen atmosphere. Upon complete addition, stirring was continued for 1 hour at reflux temperature. After cooling, the reaction mixture was decomposed with ethyl acetate, a sodium hydroxide solution 15% and 5 parts of water. The whole was filtered over diatomaceous earth and the filtrate was evaporated. The residue was purified by column chromatography over silica gel using a mixture of trichloromethane, methanol and methanol, saturated with ammonia (95:2.5:2.5 by volume) as eluent. The pure fractions were collected and the eluent was evaporated. The residue was converted into the (E)-2-butenedicate salt in 2-propanol. The salt was filtered off and dried, yielding 3.2 parts (40.5%) of 3-(2-ethoxyethyl)-N-methyl-N-(1-methyl-4-piperidinyl)-3H-imidazo[4,5-b]pyridin-2-amine (E)-2-butenedioate(2:5); mp. 153.5° C. (compound 192).

In a similar manner there was also prepared:
3-(2-ethoxyethyl)-N-(1-methyl-4-piperidinyl)-N-(phenylmethyl)-3H-imidazo[4,5-b]pyridin-2-amine hemihydrate; mp. 68.3° C. (compound 193).

C. Pharmacological Examples

The useful antihistaminic properties of the compounds of formula (I) are demonstrated in the following test procedure.

Example 54

Protection of rats from compound 440/80-induced lethality

Compound 48/80, a mixture of oligomers obtained by condensation of 4-methoxy-N-methylbenzeneethanamine and formaldehyde has been described as a potent histamine releasing agent (Int. Arch. Allergy, 13, 336 (1958)). The protection from compound 48/80-induced lethal circulatory collapse appears to be a simple way of evaluating quantitatively the antihistaminic activity of test compounds. Male rats of an inbred Wistar strain, weighing 240-260 g were used in the experiment. After overnight starvation the rats were transferred to conditioned laboratories (temp.=21±° C., relative humidity=65±5%). The rats were treated subcutaneously or orally with a test compound or with the solvent (NaCl solution, 0.9%). One hour after treatment there was injected intravenously compound 48/80, freshly dissolved in water, at a dose of 0.5 mg/kg (0.2 ml/100 g of body weight). In control experiments, wherein 250 solvent-treated animals were injected with the standard dose of compound 48/80, not more than 2.8% of the animals survived after 4 hours. Survival after 4 hours is therefore considered to be a safe criterion of a protective effect of drug administration. The $ED_{50}$-values of the compounds of formula (I) are listed in Table 1. Said $ED_{50}$-values are the values in mg/kg body weight at which the tested compounds protect 50% of the tested animals against compound 48/80-induced lethality.

TABLE 1

| Compound No. | Compound 48/80 lethality test in rats-$ED_{50}$ in mg/kg body weight |
|---|---|
| 45 | 0.02 |
| 46 | 0.01 |
| 59 | 0.02 |
| 61 | 0.04 |
| 62 | 0.04 |
| 63 | 0.04 |
| 64 | 0.02 |
| 65 | 0.02 |
| 67 | 0.02 |
| 68 | 0.04 |
| 70 | 0.04 |
| 73 | 0.01 |
| 80 | 0.02 |
| 82 | 0.04 |
| 100 | 0.04 |
| 108 | 0.04 |
| 115 | 0.04 |
| 126 | 0.04 |
| 131 | 0.02 |
| 132 | 0.01 |
| 133 | 0.02 |
| 134 | 0.005 |
| 141 | 0.02 |
| 142 | 0.04 |
| 143 | 0.02 |
| 144 | 0.02 |
| 151 | 0.02 |
| 152 | 0.005 |

(D) Composition Examples

The following formulations exemplify typical pharmaceutical compositions in dosage unit form suitable for systemic administration to animal and human subjects in accordance with the instant invention. "Active ingredient" (A.I.) as used throughout these examples relates to a compound of formula (I) or a pharmaceutically acceptable acid addition salt thereof.

Example 55: ORAL DRUGS

500 Grams of the A.I. was dissolved in 0.5 liters of 2-hydroxypropanoic acid and 1.5 liters of the polyethylene glycol at 60°-80° C. After cooling to 30°-40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

Example 56: ORAL SOLUTION 9 grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

Example 57: CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

Example 58: FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®) in about 200 milliliters of water. The wet powder mixture was sieved, dried and sieved again. Then there was added 100 grams microcrystalline cellulose (Avicel ®) and 15 grams hydrogenated vegetable oil (Sterotex ®). The whole was mixed well and compressed into tablets, giving 10,000 tablets, each containing 10 milligrams of the active ingredient.

Coating

To a solution of 10 grams methyl cellulose (Methocel 60 HG ®) in 75 milliliters of denaturated ethanol there was added a solution of 5 grams of ethyl cellulose (Ethocel 22 cps ®) in 150 milliliters of dichloromethane. Then there were added 75 milliliters of dichloromethane and 2.5 milliliters 1,2,3-propanetriol, 10 Grams of polyethylene glycol was molten and dissolved in 75 milliliters of dichloromethane. The letter solution was added to the former and then there were added 2.5 grams of magnesium octadecanoate, 5 grams of polyvinylpyrrolidone and 30 milliliters of concentrated colour suspension (Opaspray K-1-2109 ®) and the whole was homogenated. The tablet cores were coated with the thus obtained mixture in a coating apparatus.

Example 59: INJECTABLE SOLUTION 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 grams propylene glycol and 4 grams of the A.I.. The solution was cooled to room temperature and supplemented with water for injection q.s. ad 1 liter volume, giving a solution of a 4 milligrams A.I. per milliliters. The solution was sterilized by filtration (U.S.P. XVII p. 811) and filled in sterile containers.

Example 60: SUPPOSITORIES

3 Grams A.I. was dissolved in a solution of 3 grams 2,3-dihydroxybutanedioic acid in 25 milliliters polyethylene glycol 400. 12 Grams surfactant (SPAN®) and triglycerides (Witepsol 555®) q.s. ad 300 grams were molten together. The latter mixture was mixed well with the former solution. The thus obtained mixture was poured into moulds at a temperature of 37°–38° C. to form 100 suppositories each containing 30 milligrams of the active ingredient.

What is claimed is:

1. A compound of the formula:

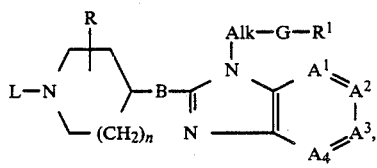
(I)

a pharmaceutically acceptable acid addition salt or a stereochemically isomeric form thereof.
wherein:
—A$^1$=A$^2$—A$^3$=A$^4$— represents a bivalent radical of the formula:

| | |
|---|---|
| —CH=CH—CH=CH— | (a-1), |
| —N=CH—CH=CH— | (a-2), |
| —CH=N—CH=CH— | (a-3), |
| —CH=CH—N=CH— | (a-4), |
| —CH=CH—CH=N— | (a-5), |
| —N=CH—N=CH— | (a-6), or |
| —CH=N—CH=N— | (a-7); | wherein one or two hydrogen atoms in said radicals (a-1)–(a-7) may, each independently from each other, be replaced by halo, $C_{1-6}$alkyl, $C_{1-6}$alkyloxy, trifluoromethyl, or hydroxy;

R$^1$ represents hydrogen; $C_{2-6}$alkenyl optionally substituted with Ar$^2$, $C_{3-6}$alkynyl, Ar$^1$, or $C_{1-6}$alkyl optionally substituted with Ar$^1$, hydroxy; $C_{1-6}$alkyloxy; carboxyl; $C_{1-6}$alkyloxycarbonyl; Ar$^2$-oxycarbonyl; or Ar$^2$-$C_{1-6}$alkyloxycarbonyl;

wherein Ar$^1$ represents a member selected from the group consisting of phenyl being optionally substituted with up to three substituents each independently selected from the group consisting of halo, hydroxy, nitro, cyano, trifluoromethyl, $C_{1-6}$alkyl, $C_{1-6}$alkyloxy, $C_{1-4}$alkylthio, mercapto, amino, mono- and di-($C_{1-6}$alkyl)amino, carboxyl, $C_{1-6}$alkyloxycarbonyl, and $C_{1-6}$alkylcarbonyl; thienyl; halothienyl; furanyl; $C_{1-6}$alkyl-substituted furanyl; pyridinyl; pyrimidinyl; pyrazinyl; thiazolyl; and imidazolyl optionally substituted with $C_{1-6}$alkyl, and wherein Ar$^2$ represents a member selected from the group consisting of phenyl being optionally substituted with up to three substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl, and $C_{1-6}$alkylcarbonyl;

G represents O, S, or NR$^2$, wherein R$^2$ represents hydrogen, $C_{1-6}$alkyl, $C_{1-6}$alkylcarbonyl, $C_{1-6}$alkyloxycarbonyl, or Ar$^2$-$C_{1-6}$alkyl wherein Ar$^2$ is as defined above;

B represents NR$^3$, CH$_2$, O, S, SO, or SO$_2$, wherein R$^3$ represents hydrogen, $C_{1-6}$alkyl, $C_{3-6}$cycloalkyl, $C_{1-6}$alkylcarbonyl, $C_{1-6}$alkyloxycarbonyl, or Ar$^2$-$C_{1-6}$alkyl wherein Ar$^2$ is as defined above;

R represents hydrogen or $C_{1-6}$alkyl;
n represents a number having a value of 0, 1, or 2;
Alk represents $C_{1-6}$alkanediyl; and
L represents hydrogen, $C_{1-6}$alkylcarbonyl, $C_{1-6}$alkylsulfonyl, $C_{1-6}$alkyloxycarbonyl, Ar$^2$-$C_{1-6}$alkyloxycarbonyl, Ar$^2$-carbonyl, Ar$^2$-sulfonyl, $C_{3-6}$cycloalkyl, $C_{2-6}$alkenyl optionally substituted with Ar$^2$ wherein each said Ar$^2$ is as defined above, $C_{1-12}$alkyl, or a radical of the formula:

| | |
|---|---|
| —Alk—R$^4$ | (b-1); |
| —Alk—Y—R$^5$ | (b-2); |
| —Alk—Z$^1$—(C=X)—Z$^2$—R$^6$ | (b-3); or |
| —CH$_2$—CHOH—CH$_2$—O—R$^7$ | (b-4), | wherein:
each Alk independently is as defined above;
R$^4$ represents Ar$^2$, Het, cyano, isocyanato, isothiocyanato, Ar$^2$-sulfonyl, or halo, wherein Ar$^2$ is as defined above;
R$^5$ represents hydrogen, Ar$^2$, Het, or $C_{1-6}$alkyl optionally substituted with halo, Ar$^2$, or Het, wherein Ar$^2$ is as defined above;
R$^6$ represents hydrogen, Ar$^2$, Het, or $C_{1-6}$alkyl optionally substituted with halo, Ar$^2$, or Het, wherein Ar$^2$ is as defined above;
R$^7$ represents Ar$^2$ or naphthalenyl wherein Ar$^2$ is as defined above;
Y represents O, S, or NR$^8$, wherein R$^8$ represents hydrogen, $C_{1-6}$alkyl, $C_{1-6}$alkylcarbonyl, or Ar$^1$-carbonyl wherein Ar$^1$ is as defined above;
Z$^1$ and Z$^2$ each independently represent O, S, NR$^9$, or a direct bond, wherein R$^9$ represents hydrogen or $C_{1-6}$alkyl; and
X represents O, S, or NR$^{10}$, wherein R$^{10}$ represents hydrogen, $C_{1-6}$alkyl, or cyano,
wherein Het represents:
(i) an optionally substituted five- or six-membered heterocyclic ring containing 1, 2, 3, or 4 heteroatoms selected from the group consisting of oxygen, sulfur, and nitrogen, provided that no more than two oxygens or sulfurs are present; or
(ii) an optionally substituted five- or six-membered heterocyclic ring containing 1 or 2 heteroatoms selected from the group consisting of oxygen, sulfur, and nitrogen, being ortho-condensed with an optionally substituted five- or six-membered ring through two ring carbon atoms or one ring carbon and one ring nitrogen atom, containing in the remainder of the condensed ring only carbon atoms; or (iii) an optionally substituted five- or six-membered heterocyclic ring containing 1 or 2 heteroatoms selected from the group consisting of oxygen, sulfur, and nitrogen, being ortho-condensed with an optionally substituted five- or six-membered heterocyclic ring through two ring carbon atoms or one ring carbon and one ring nitrogen atom, containing in the remainder of the condensed ring 1 or 2 heteroatoms selected from the group consisting of oxygen, sulfur, and nitrogen, when said Het represents a monocyclic ring system it may optionally be substituted with up to 3 substituents, and when said Het represents a bicyclic ring system it may be substituted with up to 6 substituents, wherein said substituents of Het are selected from the group consisting of a bivalent radical of the formula =X wherein X is as defined above, or a monovalent radical selected from the group consisting of halo, isocyanato, isothiocyanato, nitro, cyano, trifluoromethyl, a radical of the formula —A, a radical of the formula —Y—A, and a radical of the formula —$Z^1$—C(=X)—$Z^2$—A, wherein each A independently represents hydrogen, $Ar^2$, or $C_{1-6}$alkyl being optionally substituted with $Ar^2$, $C_{1-6}$alkoxy, $Ar^2$—O, hydroxy, or $C_{1-6}$alkyloxycarbonyl wherein $Ar^2$ is as defined above, and Y, $Z^1$, and $Z^2$ each independently are as defined above, provided that when in the radical —$Z^1$—C(=X)—$Z^2$—A, A represents hydrogen and $Z^1$ represents $NR^9$, O, or S, then $Z^2$ is other than O or S, provided that when (i) L is hydrogen, $C_{1-6}$alkyl, or benzyl, and (ii) $R^1$—G—Alk is $C_{1-6}$alkyloxyethyl, $C_{2-6}$alkenyloxyethyl, $C_{3-6}$alkynyloxyethyl, or phenoxyethyl, then —$A^1$=$A^2$—$A^3$=$A^4$— is other than a bivalent radical of formula (a-1).

2. A chemical compound according to claim 1 wherein —$A^1$=$A^2$—$A^3$=$A^4$— is a bivalent radical of formula (a-1).

3. A chemical compound according to claim 1 wherein —$A^1$=$A^2$—$A^3$=$A^4$— is a bivalent radical having a formula (a-2) through (a-7).

4. A chemical compound according to claim 1 wherein $R^1$ is hydrogen, $C_{2-6}$alkenyl, $C_{3-6}$alkynyl, $Ar^1$ or $C_{1-6}$alkyl optionally substituted with carboxyl, G is O, L is hydrogen, $C_{1-6}$alkyl or a radical of formula (b-1), (b-2) or (b-3) and B is NH or $CH_2$.

5. A chemical compound according to claim 4 wherein $R^4$, $R^5$ and $R^6$ are each $Ar^2$ or Het and $R^1$ is $C_{1-3}$alkyl optionally substituted with carboxyl, 2-propenyl or 2-propynyl.

6. A chemical compound according to claim 1 wherein the compound is 3-(2-ethoxyethyl)-N-(1-methyl-4-piperidinyl)-3H-imidazo[4,5-b]pyridin-2-amine or 3-(2-ethoxyethyl)-N̄-[1-[2-(4-methoxyphenyl)ethyl]-4-piperidinyl]-3H-imidazo[4,5-b]pyridin-2-amine.

7. An anti-allergic composition comprising one or more pharmaceutical carriers and as active ingredient an anti-allergic effective amount of at least one compound of formula (I) as claimed in claim 1.

8. An anti-allergic composition according to claim 7 wherein $R^1$ is hydrogen, $C_{2-6}$alkenyl, $C_{3-6}$alkynyl, $Ar^1$ or $C_{1-6}$alkyl optionally substituted with carboxyl, G is O, L is hydrogen, $C_{1-6}$alkyl or a radical of formula (b-1), (b-2) or (b-3) and B is NH or $CH_2$.

9. An anti-allergic composition according to claim 8 wherein $R^4$, $R^5$ and $R^6$ are each $Ar^2$ or Het and $R^1$ is $C_{1-3}$alkyl optionally substituted with carbonyl, 2-propenyl or 2-propynyl.

10. An anti-allergic composition according to claim 7 wherein the compound is 3-(2-ethoxyethyl)-N-(1-methyl-4-piperidinyl)-3H-imidazo[4,5-b]pyridin-2-amine or 3-(2-ethoxyethyl)-N̄-[1-[2-(4-methoxyphenyl)ethyl]-4-piperidinyl]-3H-imidazo[4,5-b]pyridin-2-amine.

11. A method of treating allergic diseases in warm-blooded animals suffering from the same, which method comprises the systemic administration to warm blooded animals of an effective anti-allergic amount of a compound of formula (I) as claimed in claim 1.

12. A method according to claim 11 wherein $R^1$ is hydrogen, $C_{2-6}$alkenyl, $C_{3-6}$alkynyl, $Ar^1$ or $C_{1-6}$alkyl optionally substituted with carboxyl, G is O, L is hydrogen, $C_{1-6}$alkyl or a radical of formula (b-1), (b-2) or (b-3) and B is NH or $CH_2$.

13. A method according to claim 12 wherein $R^4$, $R^5$ and $R^6$ are each $Ar^2$ or Het and $R^1$ is $C_{1-3}$alkyl optionally substituted with carboxyl, 2-propenyl or 2-propynyl.

14. A method according to claim 11 wherein the compound is 3-(2-ethoxyethyl)-N-(1-methyl-4-piperidinyl)-3H-imidazo[4,5-b]pyridin-2-amine or 3-(2-ethoxyethyl)-N̄-[1-[2-(4-methoxyphenyl)ethyl]-4-piperidinyl]-3H-imidazo[4,5-b]pyridin-2-amine.

* * * * *

UNITED STATES PATENT AND TRADEMARK OFFICE
CERTIFICATE OF CORRECTION

PATENT NO. : 4,943,580

DATED : July 24, 1990

INVENTOR(S) : Frans E. Janssens, et al.

It is certified that error appears in the above-identified patent and that said Letters Patent is hereby corrected as shown below:

Claim 1, col. 57, line 64, $C_{1-4}$alkylthio should be --$C_{1-6}$alkylthio--

Signed and Sealed this

Second Day of June, 1992

Attest:

DOUGLAS B. COMER

*Attesting Officer*     *Acting Commissioner of Patents and Trademarks*